US009102915B2

(12) United States Patent
Harmon et al.

(10) Patent No.: US 9,102,915 B2
(45) Date of Patent: Aug. 11, 2015

(54) IN VITRO EXPANSION OF POSTPARTUM-DERIVED CELLS USING MICROCARRIERS

(75) Inventors: Alexander M. Harmon, Clinton, NJ (US); L. S. Klaudyne Hong, Jersey City, NJ (US); Anthony J. Kihm, Princeton, NJ (US); Anna Gosiewska, Skillman, NJ (US)

(73) Assignee: Depuy Synthes Products, Inc., Raynham, MA (US)

( * ) Notice: Subject to any disclaimer, the term of this patent is extended or adjusted under 35 U.S.C. 154(b) by 914 days.

(21) Appl. No.: 11/939,360

(22) Filed: Nov. 13, 2007

(65) Prior Publication Data
US 2008/0166328 A1 Jul. 10, 2008

Related U.S. Application Data

(60) Provisional application No. 60/865,558, filed on Nov. 13, 2006.

(51) Int. Cl.
*C12N 5/073* (2010.01)
*C12N 5/074* (2010.01)

(52) U.S. Cl.
CPC ............ *C12N 5/0607* (2013.01); *C12N 5/0605* (2013.01); *C12N 2531/00* (2013.01); *C12N 2533/52* (2013.01); *C12N 2533/54* (2013.01)

(58) Field of Classification Search
None
See application file for complete search history.

(56) References Cited

U.S. PATENT DOCUMENTS

| | | | |
|---|---|---|---|
| 3,665,061 A | 5/1972 | Eberly, Jr. | |
| 3,393,054 A | 1/1976 | Irie | |
| 4,216,144 A | 8/1980 | Ashmead | |
| 4,290,962 A | 9/1981 | Tachi et al. | |
| 4,487,865 A | 12/1984 | Balazs et al. | |
| 4,925,677 A | 5/1990 | Feijen | |
| 4,963,489 A | 10/1990 | Naughton et al. | |
| 5,248,608 A | 9/1993 | Van Dooren et al. | |
| 5,266,476 A | 11/1993 | Sussman et al. | |
| 5,284,766 A | 2/1994 | Okano et al. | |
| 5,443,950 A | 8/1995 | Naughton et al. | |
| 6,221,904 B1 | 4/2001 | Agus et al. | |
| 7,413,734 B2 | 8/2008 | Mistry et al. | |
| 7,510,873 B2 | 3/2009 | Mistry et al. | |
| 7,524,489 B2* | 4/2009 | Messina et al. | 424/93.1 |
| 7,560,276 B2* | 7/2009 | Harmon et al. | 435/325 |
| 7,790,456 B2 | 9/2010 | Terstegge et al. | |
| 7,875,272 B2 | 1/2011 | Messina et al. | |
| 7,875,273 B2 | 1/2011 | Messina et al. | |
| 8,277,796 B2 | 10/2012 | Messina et al. | |
| 8,318,483 B2 | 11/2012 | Mistry et al. | |
| 8,703,121 B2 | 4/2014 | Harris et al. | |
| 8,815,587 B2 | 8/2014 | Harris et al. | |
| 2003/0228693 A1 | 12/2003 | Tsuzuki et al. | |
| 2003/0232752 A1 | 12/2003 | Freeman et al. | |
| 2005/0019865 A1 | 1/2005 | Kihm et al. | |
| 2005/0032209 A1 | 2/2005 | Messina et al. | |
| 2005/0037491 A1 | 2/2005 | Mistry et al. | |
| 2005/0054098 A1 | 3/2005 | Mistry et al. | |
| 2005/0058629 A1 | 3/2005 | Harmon et al. | |
| 2005/0058630 A1 | 3/2005 | Harris et al. | |
| 2005/0058631 A1 | 3/2005 | Kihm et al. | |
| 2006/0094113 A1 | 5/2006 | Epstein et al. | |
| 2006/0128014 A1 | 6/2006 | Haggblad et al. | |
| 2006/0153817 A1 | 7/2006 | Kihm et al. | |
| 2006/0153818 A1 | 7/2006 | Dhanaraj et al. | |
| 2006/0154366 A1 | 7/2006 | Brown et al. | |
| 2006/0154367 A1 | 7/2006 | Kihm et al. | |
| 2006/0182724 A1 | 8/2006 | Riordan | |
| 2006/0223177 A1 | 10/2006 | Harris et al. | |
| 2006/0233765 A1 | 10/2006 | Messina et al. | |
| 2006/0233766 A1 | 10/2006 | Messina et al. | |
| 2006/0234376 A1 | 10/2006 | Mistry et al. | |
| 2007/0009494 A1 | 1/2007 | Mistry et al. | |
| 2007/0014771 A1 | 1/2007 | Mistry et al. | |
| 2007/0036767 A1 | 2/2007 | Mistry et al. | |
| 2007/0141700 A1 | 6/2007 | Harmon | |
| 2007/0264269 A1 | 11/2007 | Harmon et al. | |
| 2010/0159588 A1 | 6/2010 | Harmon et al. | |
| 2010/0210013 A1 | 8/2010 | Mistry et al. | |
| 2010/0215714 A1 | 8/2010 | Messina et al. | |
| 2010/0247499 A1 | 9/2010 | Kihm et al. | |
| 2010/0260843 A1 | 10/2010 | Messina et al. | |
| 2010/0272803 A1 | 10/2010 | Mistry et al. | |
| 2012/0315251 A1 | 12/2012 | Harris et al. | |
| 2013/0022585 A1 | 1/2013 | Messina et al. | |
| 2014/0045263 A1 | 2/2014 | Mistry et al. | |
| 2014/0154226 A1 | 6/2014 | Messina et al. | |

FOREIGN PATENT DOCUMENTS

| | | |
|---|---|---|
| EP | 1 384 786 B2 | 1/2010 |
| WO | WO 95/23216 | 8/1995 |

(Continued)

OTHER PUBLICATIONS

Gröhn et al., "Collagen-Coated BA2+-Alginate Microcarriers for the Culture of Anchorage-Dependent Mammalian Cells," *Biotechniques*, 1997, vol. 22, pp. 970-975.

(Continued)

*Primary Examiner* — Jon P Weber
*Assistant Examiner* — Teresa E Knight
(74) *Attorney, Agent, or Firm* — Bernard F. Plantz; Johnson & Johnson

(57) ABSTRACT

Compositions and methods for the growth and expansion of mammalian cells in culture are provided. In particular, methods for the growth and expansion of postpartum-derived cells in vitro are provided using surfaces such as microcarrier beads.

24 Claims, No Drawings

(56) References Cited

FOREIGN PATENT DOCUMENTS

| WO | WO 98/17791 | 4/1998 |
|---|---|---|
| WO | WO 02/36751 | 5/2002 |
| WO | WO 02/064755 | 8/2002 |
| WO | WO 02/081723 | 10/2002 |
| WO | WO 03/070922 | 8/2003 |
| WO | WO 2004/031369 | 4/2004 |
| WO | WO 2005/001076 | 1/2005 |
| WO | WO 2005/001077 A2 | 1/2005 |
| WO | WO 2005/001078 | 1/2005 |
| WO | WO 2005/001079 | 1/2005 |
| WO | WO 2005/001080 | 1/2005 |
| WO | WO 2005/003334 | 1/2005 |
| WO | WO 2005/010162 | 2/2005 |
| WO | WO 2005/038012 | 4/2005 |
| WO | WO 2006/027229 | 3/2006 |
| WO | WO 2006/071778 | 7/2006 |
| WO | WO 2006/071794 | 7/2006 |
| WO | WO 2006/071802 | 7/2006 |
| WO | WO 2006/083394 | 8/2006 |
| WO | WO 2006/105152 | 10/2006 |
| WO | WO 2007/073552 | 6/2007 |
| WO | WO 2007/108003 | 9/2007 |
| WO | WO 2008/036447 | 3/2008 |
| WO | WO 2008/060541 A2 | 5/2008 |
| WO | WO 2008/060541 A3 | 8/2008 |
| WO | WO 2010/071862 | 6/2010 |
| WO | WO 2010/071863 A1 | 6/2010 |
| WO | WO 2010/080364 | 7/2010 |

OTHER PUBLICATIONS

Goodwin et al., "Multilineage Differentiation Activity by Cells Isolated from Umbilical Cord Blood: Expression of Bone, Fat, and Neural Markers," *Biology of Blood and Marrow Transplantation*, 2001, vol. 7, pp. 581-588.
Xu et al.,"Soft, Porous Poly(D,L lactide-co-glycotide) Microcarriers Designed for Ex Vivo Studies and for Transplantation of Adherent Cell Types including Progenitors," *Annals of the New York Academy of Sciences*,2001, vol. 944, pp. 144-159.
Newman et al., "Poly(D,L lactic-co-glycolic acid) Microspheres as Biodegradable Microcarriers for Pluripotent Stem Cells," *Biomaterials*, 2004, vol. 25, pp. 5763-5771.
Fernandes et al., "Mouse Embryonic Stem Cell Expansion in a Microcarrier-based Stirred Culture System," *Journal of Biotechnology*, 2007, vol. 132, pp. 227-236.
Covas, D.T. et al., "Isolation and Culture of Umblicial Vein Mesenchymal Stem Cells," *Brazilian Journal of Medical and Biological Research*, 2003, 36:1179-1183.
Kestendjieva, S. et al., "Characterization of Mesenchymal Stem Cells Isolated from the Human Umbilical Cord," *Cell Biology International*, 2008; 32: 724-732.
In the U.S. Patent and Trademark Office, Non-Final Office Action in re: U.S. Appl. No. 10/877,012, dated Sep. 24, 2007, 18 pages.
In the U.S. Patent and Trademark Office, Final Office Action in re: U.S. Appl. No. 10/877,012, dated Mar. 15, 2007, 13 pages.
In the U.S. Patent and Trademark Office, Non-Final Office Action in re: U.S. Appl. No. 10/877,012, dated Jul. 18, 2006, 26 pages.
In the U.S. Patent and Trademark Office, Non-Final Office Action in re: U.S. Appl. No. 10/877,446, dated Feb. 28, 2008, 19 pages.
In the U.S. Patent and Trademark Office, Final Office Action in re: U.S. Appl. No. 10/877,446, dated Jun. 27, 2007, 24 pages.
In the U.S. Patent and Trademark Office, Non-Final Office Action in re: U.S. Appl. No. 10/877,446, dated Nov. 20, 2006, 24 pages.
In the U. S. Patent and Trademark Office, Non-Final Office Action in re: U.S. Appl. No. 11/481,481, dated Mar. 20, 2009, 12 pages.
In the U. S. Patent and Trademark Office, Non-Final Office Action in re: U.S. Appl. No. 11/481,480, dated Mar. 20, 2009, 13 pages.
In the U. S. Patent and Trademark Office, Non-Final Office Action in re: U.S. Appl. No. 10/877,446 dated Jun. 12, 2009, 16 pages.
In the U. S. Patent and Trademark Office, Final Office Action in re: U.S. Appl. No. 11/481,456 dated Oct. 9, 2009, 11 pages.
In the U. S. Patent and Trademark Office, Non-Final Office Action in re: U.S. Appl. No. 11/481,456 dated May 14, 2010, 9 pages.
In the U. S. Patent and Trademark Office, Non-Final Office Action in re: U.S. Appl. No. 11/481,481 dated May 13, 2010, 9 pages.
In the U. S. Patent and Trademark Office, Non-Final Office Action in re: U.S. Appl. No. 11/481,480 dated May 17, 2010, 10 pages.
In the U. S. Patent and Trademark Office, Final Office Action in re: U.S. Appl. No. 11/481,481 dated Sep. 18, 2009, 11 pages.
In the U. S. Patent and Trademark Office, Final Office Action in re: U.S. Appl. No. 11/481,480 dated Sep. 17, 2009, 12 pages.
In the U. S. Patent and Trademark Office, Final Office Action in re: U.S. Appl. No. 10/877,446 dated Jun. 4, 2010, 17 pages.
In the U. S. Patent and Trademark Office, Non-Final Office Action in re: U.S. Appl. No. 11/481,456 dated Feb. 3, 2011, 10 pages.
In the U. S. Patent and Trademark Office, Non-Final Office Action in re: U.S. Appl. No. 11/481,481 dated Feb. 3, 2011, 10 pages.
In the U. S. Patent and Trademark Office, Non-Final Office Action in re: U.S. Appl. No. 12/389,305 dated Feb. 8, 2011, 14 pages.
In the U. S. Patent and Trademark Office, Non-Final Office Action in re: U.S. Appl. No. 11/481,480 dated Feb. 3, 2011, 10 pages.
In the U.S. Patent and Trademark Office, Final Office Action in re: U.S. Appl. No. 10/877,446 dated Nov. 2, 2011, 12 pages.
In the U.S. Patent and Trademark Office, Final Office Action in re: U.S. Appl. No. 12/389,305 dated Oct. 12, 2011, 12 pages.
In the U. S. Patent and Trademark Office, Final Office Action in re: U.S. Appl. No. 11/481,456 dated Oct. 11, 2011, 6 pages.
In the U. S. Patent and Trademark Office, Final Office Action in re: U.S. Appl. No. 10/877,446 dated Nov. 2, 2011, 12 pages.
In the U. S. Patent and Trademark Office, Final Office Action in re: U.S. Appl. No. 11/612,872 dated May 26, 2010, 11 pages.
In the U. S. Patent and Trademark Office, Non-Final Office Action in re: U.S. Appl. No. 11/612,872 dated Oct. 2, 2009, 9 pages.
U.S. Appl. No. 08/060,541, Written Opinion, May 13, 2009, Harmon et al.
Bain et al, "The Development of Large Immature Mononuclear Cells in Mixed Leukocyte Cultures," *Blood*, 1964, 23(1):106-116.
Bakhshi, et al. "Mesenchymal stem cells from the Wharton's jelly of umbilical cord segments provide stromal support for the maintenance of cord blood hematopoietic stem cells during long-term ex vivo culture", *Transfusion*, 2008; 48: 2638-2644.
Campbell, I.K. et al., "Human Articular Cartilage and Chondrocytes Produce Hemopoietic Colony-Stimulating Factors in Culture in Response to IL-1," *J. of Immun.*, 1991; 147(4):1238-1246.
Diao et al., "Human Umbilical Cord Mesenchymal Stem Cells: Osteogenesis In Vivo as Seed Cells for Bone Tissue Engineering," *J. BioMed Mater Res.*, 2009; 91A:123-131.
Diegelmann et al., "Inhibition of Collagen Secretion from Bone and Cultured Fibroblasts by Microtubular Disruptive Drugs," *Proc. Nat. Acad. Sci.*, 1972; 69(4):892-896.
Dimri, G.P. et al., "A Biomarker That Identifies Senescent Human Cells in Culture and in Aging Skin In Vivo," *Proc. Natl. Acad. Sci. USA*, 1995; 92:9363-9367.
Draper et al., "Surface Antigens of Human Embryonic Stem Cells: Changes Upon Differentiation in Culture," J. Anat., 2002; 200:249-258.
Fiegel, H.C. et al., "Liver-Specific Gene Expression in Cultured Human Hematopoietic Stem Cells," *Stem Cells*, 2003;21:98-104.
Gosiewska, A. et al., "Development of a Three-Dimensional Transmigration Assay for Testing Cell-Polymer Interactions for Tissue Engineering Applications," *Tissue Eng.*, 2001; 7:267-277.
Hayflick, L., "The Longevity of Cultured Human Cells," *J. Am. Geriatr. Soc.*, 1974; 22:1-12.
Haynesworth et al., "Cell Surface Antigens on Human Marrow-Derived Mesenchymal Cells are Detected by Monoclonal Antibodies," *Bone*, 1992; 13:69-80.
Jaffe, E.A. et al., "Culture of Human Endothelial Cells Derived From Umbilical Veins; Identification by Morphologic and Immunologic Criteria" *J Clin Invest*, 1973; 52:2745-2756.
Kadiyala, S. et al., "Culture Expanded Canine Mesenchymal Stem Cells Possess Osteochondrogenic Potential In Vivo and In Vitro," *Cell Transplant.*, 1997; 6(2):125-134.

(56) References Cited

OTHER PUBLICATIONS

Kusama et al., "Growth and morphogenesis of mouse prostate epithelial cells in collagen gel matrix culture" *Cell Biol Int Rep*, 1989; 13:569-575.

McAdams, T.A., et al., "Hematopoietic Cell Culture Therapies (Part I): Cell Culture Considerations," *TibTech*, 1996; 14:341-349.

Mackay, A.M. et al., "Chondrogenic Differentiation of Cultured Human Mesenchymal Stem Cells From Marrow," *Tissue Engineering*, 1998; 4(4):415-428.

Makino, S. et al., "Cardiomyocytes can be generated from marrow stromal cells in vitro," *J. Clin. Invest.*, 1999; 103:697-705.

Mitchell, K.E. et al., "Matrix Cells From Wharton's Jelly Form Neurons and Glia," *Stem Cells*, 2003; 21:50-60.

Naughton et al., "Cells isolated from Wharton's jelly of the human umbilical cord develop a cartilage phenotype when treated with TGF-b in vitro," 1997; *FASEB J* 11:A19 (Abstract 108).

Rahman, Z. et al., "Isolation and Primary Culture Urothelial Cells from Normal Human Bladder," *Urol. Research*, 1987; 15:315-320.

Rickard, D.J. et al., "Induction of Rapid Osteoblast Differentiation in Rat Bone Marrow Stromal Cell Cultures by Dexamethasone and BMP-2," *Dev. Biol.*, 1994; 161:218-228.

Romanov, Y.A. et al., "Searching for Alternative Sources of Postnatal Human Mesenchymal Stem Cells: Candidate MSC-Like Cells from Umbilical Cord," *Stem Cells*, 2003; 21:105-110.

Seaver et al. "The chick oviduct in tissue culture. I. Initial characterization of growing primary oviduct tissue cultures," *Exp. Cell Res.*, 1984; 155: 241-251.

Shuto, T. et al., "Dexamethasone Stimulates Osteoclast-Like Cell Formation by Inhibiting Granulocyte-Macrophage Colony-Stimulating Factor Production in Mouse Bone Marrow Cultures," *Endocrinology*, 1994; 134(3):1121-1126.

Ulloa-Montoya, F. et al., "Culture Systems for Pluripotent Stem Cells," *Journal of Bioscience and Bioengineering*, 2005; 100(1):12-27.

Wang, Y. et al., "Enhanced Recovery of Hematopoietic Progenitor and Stem Cells from Cultivated, Postpartum Human Placenta," *Blood*, 2001; 98(11): 183a (Abstract 769).

Zhang, Y. et al., "Human placenta-derived mesenchymal progenitor cells support culture expansion of long-term culture-initiating cells from cord blood CD34+ cells," *Exp Hematol*, 2004; 32: 657-64.

Baksh, D. et al., "Comparison of proliferative and multilineage differentiation potential of human mesenchymal stem cells derived from umbilical cord and bone marrow." *Stem Cells*, 2007; 25: 1384-1392.

Ciavarella, S. et al., "Umbilical Cord Mesenchymal Stem Cells: Role of Regulatory Genes in Their Differentiation to Osteoblasts," *Stem Cells and Development*, 2009; 18:1211-1220.

Covas, D.T. et al., "Isolation and culture of umbilical vein mesenchymal stem cells." *Brazilian Journal of Medical and Biological Research*, 2003; 36: 1179-1183.

Hass, R. et al., "Different populations and sources of human mesenchymal stem cells (MSC): A comparison of adult and neonatal tissue-derived MSC," *Cell Communication and Signaling*, 2011; 9:12, p. 1-14.

Henderson, GI, et al., "Inhibition of Placental Valine Uptake after Acute and Chronic Maternal Ethanol Consumption", J Pharmacol Exp Therap, 1981; 216:465-472.

Mattsson, J. et al. "Graft Failure after Allogenic Hematopoietic Cell Transplantation," *Biol Blood Marrow Transplant*, 2008; 14 (Supplement 1): 165-170.

Rachakatla, R. S. et al., "Development of Human Umbilical Cord Matrix Stem Cell-Based Gene Therapy for Experimental Lung Tumors," *Cancer Gene Therapy*, 2007; 14:828-835.

Secco, M. et al., "Multipotent Stem Cells from Umbilical Cord: Cord is Richer than Blood!" *Stem Cells*, 2008; 26:146-150.

Troyer, D. L. et al., "Concise Review: Wharton's Jelly-Derived Cells Are a Primitive Stromal Cell Population," *Stem Cells*, 2008; 26:591-599.

Voet D and Voet JG, Biochemistry (2d Ed., John Wiley & Sons), 1995; Chapter 4. Amino Acids: B. The Fischer Convention, p. 64.

* cited by examiner

IN VITRO EXPANSION OF POSTPARTUM-DERIVED CELLS USING MICROCARRIERS

CROSS REFERENCE TO RELATED APPLICATION

This application claims benefit under 35 U.S.C. §119(e) of U.S. Application No. 60/865,558, filed Nov. 13, 2006, the entirety of which is incorporated herein by reference.

FIELD

The invention relates generally to the growth and expansion of mammalian cells. In particular, the invention relates to methods for the growth and expansion of mammalian postpartum-derived cells (PPDCs) in vitro using surfaces or particles, such as microcarrier particles, pellets, or beads.

BACKGROUND

Commercial cell therapy products are preferably produced in aseptic systems that are closed. However, the growth of many cell types used for commercial cell therapy product is anchorage-dependent.

While stirred tank reactors, shaker flasks, spinner flasks, uplift reactors, and the like, are all useful for cells that grow in suspension (e.g. hybridomas for monoclonal antibody production, many cells used for recombinant DNA technology, and most insect cell cultures), the options for growing and expanding anchorage-dependent cells are more limited.

Included among the anchorage-dependent cells are many normal diploid cell strains, as well as most primary cell types. Options for large-scale production of such cells include roller bottles, fiber beds, hollow fiber systems, multi-plate or stacked-plate culture systems, cell cubes, and microcarriers, each of which has advantages and disadvantages.

Microcarrier-based methods of cell culture provide many advantages including ease of downstream processing in many applications. Microcarriers are typically roughly spherical in shape, and can be either macro- or micro-porous, or solid. The use of microcarriers for cell attachment facilitates the use of stirred tank and related reactors for growth of anchorage-dependent cells. The cells attach to the readily suspended microparticles. The requirement for suspendability limits the physical parameters of the microcarriers themselves. Thus, microcarriers commonly have a mean diameter in the range of 50-2000 microns. In some applications solid-type microcarriers range from about 100 to about 250 microns whereas porous-type microcarrier beads range from about 250 to about 2500 microns. These size ranges allow for selection of microcarriers which are large enough to accommodate many anchorage-dependent cells, while small enough to form suspensions with properties suitable for use in stirred reactors.

Both porous and solid types of microparticulate carriers are commercially available from suppliers. Examples of commercially available microcarriers include Cytodex® 1 and Cytodex® 3, which are both dextran-based microcarriers from GE Healthcare Life Sciences. Porous microcarriers on the market include CYTOLINE as well as Cytopore® products also from GE Healthcare Life Sciences. Biosilon® (NUNC) and Cultispher® (Percell Biolytica) are also commercially available.

Although for some types of cells, the morphology of cells grown on highly curved surfaces, such as those provided by microcarriers, can be an issue, generally microcarriers provide many advantages in terms of large-scale growth including ease of harvesting cells, and ease of separating useful extracellular products from the cells themselves. A need exists in the art for an efficient and high yield method to grow and harvest anchorage dependent cells such as postpartum cells derived from umbilical cord or placenta.

SUMMARY

The present invention provides compositions and methods for growth and expansion of mammalian cells. Methods are provided for the growth and expansion of postpartum-derived mammalian cells in vitro utilizing surfaces such as microcarrier beads or porous microcarrier beads. The mammalian cells are anchorage-dependent postpartum-derived mammalian cells, for example, umbilical-derived cells or placental-derived cells.

A method of culturing anchorage-dependent postpartum cells is provided which comprises providing at least one anchorage-dependent postpartum cell, providing a cell growth medium for growing the postpartum cell, providing at least one carrier particle for attachment of the anchorage-dependent postpartum cell, and contacting the anchorage-dependent cell with the carrier particle in the presence of the growth medium under conditions permitting attachment and growth of the cell, thereby culturing the anchorage-dependent postpartum cell.

The method for culturing anchorage-dependent postpartum cells provides culturing the cells on at least one carrier particle, for example, a microcarrier. The microcarrier can be comprised of natural or synthetically-derived materials. Examples include collagen-based microcarriers, dextran-based microcarriers, or cellulose-based microcarriers, as well as glass, ceramics, polymers, or metals. The microcarrier can be protein-free or protein-coated, for example, with collagen. In a further aspect the microcarrier can be comprised of, or coated with, compounds that enhance binding of the cell to the microcarrier and enhance release of the cell from the microcarrier including, but not limited to, poly (monostearoylglyceride co-succinic acid), poly-D,L-lactide-co-glycolide, sodium hyaluronate, collagen, fibronectin, laminin, elastin, lysine, n-isopropyl acrylamide, vitronectin. Examples further include microcarriers that possess a microcurrent, such as microcarriers with a particulate galvanic couple of zinc and copper that produces low levels of biologically relevant electricity; or microcarriers that are paramagnetic, such as paramagnetic calcium-alginate microcarriers. In a further aspect the method provides a second cell type co-cultured with the anchorage-dependent postpartum cells.

The method for culturing anchorage-dependent postpartum cells provides culturing the cells to result in at least about five population doublings over about twenty days. The method for culturing anchorage-dependent postpartum cells provides culturing the cells to result in at least about seven and one half population doublings over about twenty days.

Compositions are provided comprising anchorage-dependent postpartum cells cultured by the methods which utilize carrier particles, e.g., microcarrier particles or porous microcarrier particles, for attachment to the cells. The anchorage-dependent postpartum cells are phenotypically the same as cells grown in static cultures as determined for one or more of the markers CD10, CD13, CD31, CD34, CD44, CD45, CD73, CD90, CD117, CD141, PDGFr-α, HLA-A, HLA-B, HLA-C, HLA-DR, HLA-DP, and HLA-DQ. In a further aspect, the anchorage-dependent postpartum cells are phenotypically CD10+, CD13+, CD31−, CD34−, CD44+, CD45−, CD73+, CD90+, CD117−, CD141−, PDGFr-α+, HLA-A+, HLA-B+, HLA-C+, HLA-DR−, HLA-DP−, and HLA-DQ−. A bioreactor is provided comprising the anchorage-dependent postpartum cells cultured on carrier particles. A composition for cell therapy is provided utilizing the anchorage-dependent postpartum cells cultured on carrier particles.

DETAILED DESCRIPTION

Overview

The present invention provides compositions and methods for growth and expansion of mammalian cells. Methods are provided for the growth and expansion of postpartum-derived mammalian cells in vitro utilizing surfaces such as microcarrier beads or porous microcarrier beads. The mammalian cells are anchorage-dependent postpartum-derived mammalian cells, for example, umbilical-derived cells or placental-derived cells.

A method for culturing anchorage-dependent postpartum cells is provided which comprises providing at least one anchorage-dependent postpartum cell, providing a cell growth medium for growing the postpartum cell, providing at least one carrier particle for attachment of the anchorage-dependent postpartum cell, and contacting the anchorage-dependent cell with the carrier particle in the presence of the growth medium under conditions permitting attachment and growth of the cell, thereby culturing the anchorage-dependent postpartum cell.

The method for culturing anchorage-dependent postpartum cells provides culturing the cells on at least one carrier particle, for example, a microcarrier. The microcarrier can be comprised of natural or synthetically-derived materials. Examples include collagen-based microcarriers, dextran-based microcarriers, or cellulose-based microcarriers, as well as glass, ceramics, polymers (such as polystyrene), or metals. The microcarrier can be protein-free or protein-coated, for example, with collagen. In a further aspect the microcarrier can be comprised of, or coated with, compounds that enhance binding of the cell to the microcarrier and enhance release of the cell from the microcarrier including, but not limited to, poly(monostearoylglyceride co-succinic acid), poly-D,L-lactide-co-glycolide, sodium hyaluronate, fibronectin, laminin, elastin, lysine, n-isopropyl acrylamide, vitronectin, and collagen. Examples further include microcarriers that possess a microcurrent, such as microcarriers with a particulate galvanic couple of zinc and copper that produces low levels of biologically relevant electricity; or microcarriers that are paramagnetic, such as paramagnetic calcium-alginate microcarriers.

Compositions are provided comprising anchorage-dependent postpartum cells cultured by the methods which utilize carrier particles, e.g., microcarrier particles, porous microcarrier particles, microcarriers that possess a microcurrent, or paramagnetic microcarriers, for attachment to the cells. The anchorage-dependent postpartum cells may be phenotypically the same as cells grown in static T-flasks as determined for one or more of the markers CD10, CD13, CD31, CD34, CD44, CD45, CD73, CD90, CD117, CD141, PDGFr-α, HLA-A, HLA-B, HLA-C, HLA-DR, HLA-DP, and HLA-DQ. In a further aspect, the anchorage-dependent postpartum cells are phenotypically CD10+, CD13+, CD31−, CD34−, CD44+, CD45−, CD73+, CD90+, CD117−, CD141−, PDGFr-α+, HLA-A+, HLA-B+, HLA-C+, HLA-DR−, HLA-DP−, and HLA-DQ−. In one embodiment, the anchorage dependent postpartum cells are phenotypically CD13+, CD90+, CD34−, and CD117−. In a further embodiment, the anchorage-dependent postpartum cells are phenotypically CD10+, CD13+, CD44+, CD73+, CD90+ PDGFr-α+, PD-L2+, HLA-A+, HLA-B+, HLA-C+, and CD31−, CD34− CD45−, CD80−, CD86−, CD117−, CD141−, CD178−, B7-H2, HLA-G−, HLA-DR−, HLA-DP−, and HLA-DQ−.

It is to be understood that this invention is not limited to particular methods, reagents, compounds, compositions or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a cell" includes a combination of two or more cells, and the like.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

The cells cultured in the methods described herein are referred to as "postpartum-derived cells (PPDCs)" or "postpartum cells." Subsets of the cells of the present invention are referred to as "placenta-derived cells (PDCs)" or "human Umbilical Tissue-derived Cells (hUTCs)." In addition, the cells may be described as being stem or progenitor cells, the latter term being used in the broad sense. The term "derived" is used to indicate that the cells have been obtained from their biological source and grown or otherwise manipulated in vitro (e.g., cultured in a growth medium to expand the population and/or to produce a cell line). The in vitro manipulations of postpartum-derived cells and the unique features of the postpartum-derived cells of the present invention are described in detail below.

Various terms are used to describe cells in culture. "Cell culture" refers generally to cells taken from a living organism and grown under controlled conditions ("in culture"). A "primary cell culture" is a culture of cells, tissues or organs taken directly from organisms and before the first subculture. Cells are "expanded" in culture when they are placed in a growth medium under conditions that facilitate cell growth and/or division, resulting in a larger population of the cells. When cells are expanded in culture, the rate of cell proliferation is sometimes measured by the amount of time needed for the cells to double in number. This is referred to as "doubling time."

A "cell line" is a population of cells formed by one or more subcultivations of a primary cell culture. Each round of subculturing is referred to as a passage. When cells are subcultured, they are referred to as having been "passaged." A specific population of cells, or a cell line, is sometimes referred to or characterized by the number of times it has been passaged. For example, a cultured cell population that has been passaged ten times may be referred to as a "P10" culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including, but not limited to the seeding density, substrate, medium, and time between passaging.

A "conditioned medium" is a medium in which a specific cell or population of cells has been cultured, and then removed. While the cells are cultured in the medium, they secrete cellular factors that can provide trophic support to other cells. Such trophic factors include, but are not limited to hormones, cytokines, extracellular matrix (ECM), proteins, vesicles, antibodies, and granules. The medium containing the cellular factors is the conditioned medium.

Generally, a "trophic factor" is defined as a substance that promotes survival, growth, proliferation, maturation, differentiation, and/or maintenance of a cell, or stimulates increased activity of a cell. "Trophic support" is used herein to refer to the ability to promote survival, growth, proliferation, maturation, differentiation, and/or maintenance of a cell, or to stimulate increased activity of a cell.

When referring to cultured vertebrate cells, the term senescence (also "replicative senescence" or "cellular senescence") refers to a property attributable to finite cell cultures; namely, their inability to grow beyond a finite number of population doublings (sometimes referred to as "Hayflick's limit"). Although cellular senescence was first described using fibroblast-like cells, most normal human cell types that can be grown successfully in culture undergo cellular senescence. The in vitro lifespan of different cell types varies, but the maximum lifespan is typically fewer than 100 population doublings (this is the number of doublings for all the cells in the culture to become senescent and thus render the culture unable to divide). Senescence does not depend on chronological time, but it is measured by the number of cell divisions, or population doublings, the culture has undergone. Thus, cells made quiescent by removing essential growth factors may still be able to resume growth and division when the growth factors are re-introduced, and thereafter carry out the same number of doublings as equivalent cells grown continuously. Similarly, when cells are frozen in liquid nitrogen after various numbers of population doublings and then thawed and cultured, they undergo substantially the same number of doublings as cells maintained unfrozen in culture. Senescent cells are not dead or dying cells; they are actually resistant to both cell division and programmed cell death (apoptosis), and can be maintained in their nondividing state indefinitely. These cells are very much alive and metabolically active, but they do not divide. The nondividing state of senescent cells has not yet been found to be reversible by any biological, chemical, or viral agent.

"Growth medium" refers to a culture medium sufficient for expansion of postpartum-derived cells. Growth medium preferably contains Dulbecco's Modified Essential Media (DMEM). More preferably, Growth medium contains glucose. Growth medium preferably contains DMEM-low glucose (DMEM-LG) (Invitrogen, Carlsbad, Calif.). Growth medium preferably contains about 15% (v/v) serum (e.g., fetal bovine serum, defined bovine serum). Growth medium preferably contains at least one antibiotic agent and/or antimycotic agent (e.g., penicillin, streptomycin, amphotericin B, gentamicin, nystatin; preferably, 50 units/milliliter penicillin G sodium and 50 micrograms/milliliter streptomycin sulfate). Growth medium preferably contains 2-mercaptoethanol (Sigma, St. Louis Mo.). Most preferably, Growth medium contains DMEM-low glucose, serum, 2-mercaptoethanol, and an antibiotic agent.

"Standard growth conditions" refers to standard atmospheric conditions comprising about 5% $CO_2$, a temperature of about 35-39° C., more preferably 37° C., and a relative humidity of about 100%.

"Isolated" refers to a cell, cellular component, or a molecule that has been removed from its native environment.

"Anchorage-dependent cells" are cells, including mammalian cells, that need to attach to a surface, e.g., a tissue culture flask surface or a microcarrier particle surface, to replicate in tissue culture.

"Microcarriers" refers to particles, beads, or pellets useful for attachment and growth of anchorage dependent cells in culture. The microcarriers have the following properties: (a) They are small enough to allow them to be used in suspension cultures (with a stirring rate that does not cause significant shear damage to the microcarriers or the cells); (b) They are solid, or have a solid core with a porous coating on the surface; and (c) Their surfaces (exterior and interior surface in case of porous carriers) may be positively or negatively charged. In one aspect, the microcarriers have an overall particle diameter between about 150 and 350 μm, and have a positive charge density of between about 0.8 and 2.0 meq/g. Useful microcarriers include, without limitation, Cytodex 1®, Cytodex 2®, or Cytodex 3® (GE Healthcare Life Sciences).

In another aspect, the microcarrier is a solid carrier. Solid carriers are particularly suitable for adhesion cells, e.g., anchorage-dependent cells. The carrier particle can also be a porous microcarrier. Examples further include microcarriers that possess a microcurrent, such as microcarriers with a particulate galvanic couple of zinc and copper that produces low levels of biologically relevant electricity; or microcarriers that are paramagnetic, such as paramagnetic calcium-alginate microcarriers.

"Porous microcarriers" refers to particles useful for attachment and growth of anchorage-dependent cells in culture. The porous microcarriers have the following properties: (a) they are small enough to allow them to be used in suspension cultures (with a stirring rate that does not cause significant shear damage to the microcarriers or the cells); (b) they have pores and interior spaces of sufficient size to allow cells to migrate into the interior spaces of the particle and (c) their surfaces (exterior and interior) may be positively or negatively charged. In one series of embodiments, the carriers (a) have an overall particle diameter between about 150 and 350 μm; (b) have pores having an average pore opening diameter of between about 15 and about 40 μm; and (c) have a positive charge density of between about 0.8 and 2.0 meq/g. In some embodiments, the positive charge is provided by DEAE (N,N,-diethylaminoethyl) groups. Useful porous microcarriers include, without limitation, Cytopore 1® and Cytopore 2® (GE Healthcare Life Sciences, Piscataway N.J.).

The subject invention demonstrates for the first time the methods for isolation and culture of cells from postpartum tissue including umbilicus and placenta that can be expanded in vitro to large numbers on microcarrier particles or porous microcarrier particles. The anchorage-dependent postpartum cells are capable of differentiating into a mesodermal, or ectodermal or endodermal lineage.

The anchorage-dependent postpartum cells of the invention have the capacity to differentiate into any one or more tissue types including, but not limited to, mesodermal tissues, such as mature adipose tissue, bone, cartilage, various tissues of the heart (e.g., pericardium, epicardium, epimyocardium, myocardium, pericardium, valve tissue), dermal connective tissue, hemangial tissues (e.g., corpuscles, endocardium, vascular epithelium), hematopoetic tissue, muscle tissues (including skeletal muscles, cardiac muscles, smooth muscles), urogenital tissues (e.g., kidney, pronephros, meta- and mesonephric ducts, metanephric diverticulum, ureters, renal pelvis, collecting tubules), epithelium of the female reproductive structures (particularly the oviducts, uterus, and vagina), mesodermal glandular tissues (e.g., adrenal cortex tissues), and stromal tissues (e.g., bone marrow). Of course, in as much as the postpartum cells can retain potential to develop into a mature cell, it also can realize its developmental phenotypic potential by differentiating into an appropriate precursor cell (e.g., a preadipocyte, a premyocyte, a preosteocyte).

Postpartum cells or cells derived from them may be used in tissue repair, regeneration or augmentation for any tissue of the body. In addition the cells of the current invention may be used for trophic support.

Isolation of Cells from Postpartum Tissue

Methods for isolating and collecting PPDCs are described in copending U.S. Publication No. 2005-0054098 and U.S. Publication No. 2005-0058631, incorporated herein by reference in their entirety. To collect postpartum umbilicus and placenta for the isolation and culture of cells on carrier particles, placenta and umbilicus is obtained immediately post childbirth. For example, but not by way of limitation, following removal of the amniotic membrane the placenta or umbilical cord (drained of blood), or a section thereof, may be transported from the birth site to the laboratory in a sterile container such as a flask, beaker or culture dish, containing a salt solution or medium, such as, for example, Dulbecco's Modified Eagle's Medium (DMEM). The umbilical cord is preferably maintained and handled under sterile conditions prior to and during collection of the tissue, and may additionally be surface-sterilized by brief surface treatment of the cord with, for example, a 70 percent by volume ethanol in water solution, followed by a rinse with sterile, distilled water or isotonic salt solution. The umbilical cord can be briefly stored for about 1 to 24 hours at about 3° to about 50° C. It is preferable to keep the tissue at 4° to 10° C., but not frozen, prior to extraction of cells. Antibiotic or antimycotics may be included in the medium to reduce microbiological contamination. Cells are collected from the umbilical cord and placenta under sterile conditions by any appropriate method known in the art. These examples include digestion with enzymes such as dispase, collagenase, trypsin, hyaluronidase, or dissection or mincing. Isolated cells or tissue pieces from which cells grow out may be used to initiate cell cultures.

The postpartum tissue may be rinsed with anticoagulant solution such as heparin. The tissue may be transported in solutions used for transportation of organs used for transplantation such as University of Wisconsin solution or Perfluorochemical solution.

Culture of Postpartum Cells

Isolated cells are transferred to sterile tissue culture vessels either uncoated or coated with extracellular matrix or ligands such as laminin, collagen, gelatin. To grow the cells culture media is added such as, DMEM (high or low glucose), McCoys 5A medium, Eagle's basal medium, CMRL medium, Glasgow minimum essential medium, Ham's F-12 medium (F12), Iscove's modified Dulbecco's medium, Liebovitz L-15 medium, MCDB, and RPMI 1640, among others. The culture medium may be supplemented with one or more components including, for example, fetal bovine serum (FBS), equine serum (ES), human serum (HS), growth factors, for example PDGF, FGF, erythropoietin and one or more antibiotics and/or antimycotics to control microbial contamination, such as, penicillin G, streptomycin sulfate, amphotericin B, gentamicin, and nystatin, either alone or in combination, among others.

The cells in culture vessels at a density to allow cell growth are placed in an incubator with 0 to 5 percent by volume $CO_2$ in air and 2 to 25 percent $O_2$ in air at 25 to 40° C. The medium in the culture vessel can be static or agitated, for example using a bioreactor. Cells may be grown under low oxidative stress (e.g. with addition of glutathione, Vitamin C, Catalase, Vitamin E, N-Acetylacysteine). "Low oxidative stress", as used herein, refers to conditions of no or minimal free radical damage to the cultured cells. Cells may also be grown under alternating conditions, for example, in a period of normoxia followed by a period of hypoxia.

Methods for the selection of the most appropriate culture medium, medium preparation, and cell culture techniques are well known in the art and are described in a variety of sources, including Doyle et al., (eds.), 1995, *Cell & Tissue Culture: Laboratory Procedures*, John Wiley & Sons, Chichester; and Ho and Wang (eds.), 1991, *Animal Cell Bioreactors*, Butterworth-Heinemann, Boston, which are incorporated herein by reference in their entirety.

After culturing the isolated cells or tissue pieces for a sufficient period of time, for example, about 10 to about 12 days, postpartum cells present in the explanted tissue will tend to have grown out from the tissue, either as a result of migration there from or cell division, or both. Postpartum cells may then be removed to a separate culture vessel containing fresh medium of the same or a different type as that used initially, where the population of cells can be mitotically expanded.

Alternatively, the different cell types present in postpartum tissue can be fractionated into subpopulations from which the postpartum cells can be isolated. This may be accomplished using standard techniques for cell separation including, but not limited to, enzymatic treatment to dissociate postpartum tissue into its component cells, followed by cloning and selection of specific cell types, using either morphological or biochemical markers, selective destruction of unwanted cells (negative selection), separation based upon differential cell agglutinability in the mixed population as, for example, with soybean agglutinin, freeze-thaw procedures, differential adherence properties of the cells in the mixed population, filtration, conventional and zonal centrifugation, centrifugal elutriation (counter-streaming centrifugation), unit gravity separation, countercurrent distribution, electrophoresis, and fluorescence activated cell sorting (FACS). For a review of clonal selection and cell separation techniques, see Freshney, R. I., *Culture of Animal Cells; A Manual of Basic Techniques*, $4^{th}$ Ed., Wiley-Liss, Inc., New York, 2000, which is incorporated herein by reference in its entirety.

The medium is changed as necessary by carefully aspirating the medium from the dish, for example, with a pipette, and replenishing with fresh medium. Incubation is continued as described above until a sufficient number or density of cells accumulate in the dish, for example, approximately 70 percent confluence. The original explanted tissue sections may be removed and the remaining cells are trypsinized using standard techniques or using a cell scraper. After trypsinization, the cells are collected, removed to fresh medium and incubated as described above. The medium may be changed at least once at 24 hours post-trypsin to remove any floating cells. The cells remaining in culture are postpartum cells.

Postpartum cells can be characterized using flow cytometry, immunohistochemistry, gene arrays, PCR, protein arrays or other methods known in the art.

Postpartum cells can undergo at least 10 population doublings. One of skill in the art would be able to determine when a cell has undergone a population doubling (Freshney, R. I. *Culture of Animal Cells: A Manual of Basic Techniques* 4th Ed., Wiley-Liss, New York, 2000).

While a postpartum cell can be isolated, preferably it is within a population of cells. The invention provides a defined population of postpartum cells. In one embodiment, the population is heterogeneous. In another embodiment, the population is homogeneous.

In yet another embodiment, a population of postpartum cells can support cells for culturing other cells. For example, cells that can be supported by PPDC populations may include other types of stem cells, such as neural stem cells (NSC), hematopoetic stem cells (HPC, particularly $CD34^+$ stem cells), embryonic stem cells (ESC) and mixtures thereof. In other embodiments, the population is substantially homogeneous, consisting essentially of PPDCs.

The anchorage-dependent postpartum cells cultured on microcarrier particles or porous microparticles have been phenotypically characterized as the same as cells grown in static cultures for one or more of the markers CD10, CD13, CD31, CD34, CD44, CD45, CD73, CD90, CD117, CD141, PDGFr-α, HLA-A, HLA-B, HLA-C, HLA-DR, HLA-DP, and HLA-DQ. In a further aspect, the anchorage-dependent postpartum cells have been characterized as having a phenotype comprising CD10+, CD13+, CD31−, CD34−, CD44+, CD45−, CD73+, CD90+, CD117−, CD141−, PDGFr-α+, HLA-A+, HLA-B+, HLA-C+, HLA-DR−, HLA-DP−, and HLA-DQ−. In one embodiment, the anchorage dependent postpartum cells are phenotypically CD13+, CD90+, CD34−, and CD117−. In a further embodiment, the anchorage-dependent postpartum cells are phenotypically CD10+, CD13+, CD44+, CD73+, CD90+ PDGFr-α+, PD-L2+, HLA-A+, HLA-B+, HLA-C+, and CD31−, CD34− CD45−, CD80−, CD86−, CD117−, CD141−, CD178−, B7-H2, HLA-G−, HLA-DR−, HLA-DP−, and HLA-DQ−.

Postpartum cells can be used for screening natural or synthetic libraries of compounds or peptides for molecules that effect differentiation or signaling pathways including kinases for example Jak, MAP, Jun, p38 Akt, PKC, calmodulin, tyrosine kinase, SMAD, ERK, JNK, MEK, ErbB, FAK and PI3.

Postpartum cells can be characterized further by using gene chip analysis or antibody arrays.

Microcarriers for Cell Culture

Microcarrier culture is a technique which makes possible the practical high yield culture of anchorage-dependent cells, for example, anchorage-dependent postpartum cells. Microcarriers have been specifically developed for the culture of cells, such as mammalian postpartum cells, in culture volumes ranging from a few milliliters to greater than one thousand liters. The microcarrier is biologically inert and provides a strong but non-rigid substrate for stirred microcarrier cultures. The microcarriers may be transparent, allowing microscopic examination of the attached cells. Cytodex 3® (GE Healthcare Life Sciences, Piscataway N.J.) consists of a thin layer of denatured collagen chemically coupled to a matrix of crosslinked dextran. The denatured collagen layer on Cytodex 3® is susceptible to digestion by a variety of proteases, including trypsin and collagenase, and provides the ability to remove cells from the microcarriers while maintaining maximum cell viability, function, and integrity.

Protein free microcarriers can be used to culture postpartum cells. For example, microcarrier beads for use in manufacturing and laboratory or research use sold under the tradename HILLEX® (SoloHill Engineering, Inc., Ann Arbor, Mich.) are modified polystyrene beads with cationic trimethyl ammonium attached to the surface to provide a positively charged surface to the microcarrier. The bead diameter ranges from about 90 to about 200 microns in diameter.

Microcarrier-based methods of cell culture provided many advantages including ease of downstream processing in many applications. Microcarriers are typically roughly spherical in shape, and can be either porous or solid. The use of microcarriers for cell attachment facilitates the use of stirred tank and related reactors for growth of anchorage-dependent cells. The cells attach to the readily suspended microparticles. The requirement for suspendability limits the physical parameters of the microcarriers. Thus, microcarriers commonly have a mean diameter in the range of 50-2000 microns. In some applications solid-type microcarriers range from about 100 to about 250 microns whereas porous-type microcarrier beads range from about 250 to about 2500 microns. These size ranges allow for selection of microcarriers which are large enough to accommodate many anchorage-dependent cells, while small enough to form suspensions with properties suitable for use in stirred reactors.

Among the factors considered in using microcarrier beads and the like are: attachment efficiency, immunogenicity, biocompatibility, ability to biodegrade, time to reach confluence, the growth parameters of attached cells including maximum attainable density per unit surface area, detachment techniques where required, and the efficiency of the detachment, scalability of the culture conditions as well as homogeneity of the culture under scaled-up conditions, the ability to successfully scale-up detachment procedures, and whether the beads will be used for implantation. These considerations can be influenced by the surface properties of the microcarrier beads, as well as by the porosity, diameter, density, and handling properties of the microcarrier.

For example, the density of the microcarrier particles or beads is a consideration. Excessive density may cause the microcarrier particles or beads to settle out of the suspension, or tend to remain completely towards the bottom of the culture vessel, and thus may result in poor bulk mixing of the cells, culture medium and gaseous phases in the reactor. On the other hand, a density that is too low may result in excessive floating of the microcarrier. A density of 1.02 to 1.15 $g/cm^3$ is typical of many microcarrier beads.

The small diameter of microcarrier particles and the volume of particles that can be added to a reactor allows the microcarriers to contribute substantial surface area in vast excess to that found in roller bottles or other methods of growing anchorage-dependent cells, e.g. on plates. Porous microcarriers provide even greater surface area per unit volume or weight. These porous microcarriers possess large cavities that are available for the growth of anchorage-dependent cells. These cavities increase the surface area greatly, and may protect cells from detrimental mechanical effects, such as shear stress, for example from mixing or from gas sparging. Methods for maximizing growth of postpartum cells in roller bottles is described in U.S. Application Ser. No. 60/751, 550, filed Dec. 19, 2005, which is incorporated herein by reference in its entirety.

The microcarrier surface may be textured to enhance cell attachment and proliferation. The microcarrier surface texture be achieved by techniques including, but not limited to, molding, casting, leeching and etching. The resolution of the features of the textured surface may be on the nanoscale. The textured surface may be used to induce a specific cell alignment on the microcarrier surface. The surface of the pores within the porous microcarriers may also be textured to enhance cell attachment and proliferation. Pore surface texture be achieved by techniques such as but not limited to molding, casting, leeching and etching.

The microcarrier surface may be plasma-coated to impart a specific charge to microcarrier surfaces. These charges may enhance cell attachment and proliferation.

In other embodiments, the microcarriers are composed of, or coated with, thermoresponsive polymers such as poly-N-isopropylacrylamide, or have electromechanical properties.

The microcarriers may possess a microcurrent, such as microcarriers with a particulate galvanic couple of zinc and copper that produces low levels of biologically relevant electricity. The microcarriers may be paramagnetic, such as paramagnetic calcium-alginate microcarriers.

Both porous and solid types of microparticulate carriers are commercially available from suppliers. Examples of commercially available solid microcarriers include Cytodex® 1 and Cytodex® 3, which are both dextran-based microcarriers from GE Healthcare Life Sciences. Porous microcarriers on the market include CYTOLINE as well as Cytopore® products also from GE Healthcare Life Sciences. Biosilon® (NUNC) and Cultispher® (Percell Biolytica) are also commercially available.

The carrier particles may also contain a bioactive agent. The carrier particle may also contain a bioactive agent that may regulate the growth or function of cells or the tissue milieu these factors may include but are not limited to fibroblast growth factors, erythropoietin, vascular endothelial cell growth factors, platelet derived growth factors, bone morphogenic proteins, transforming growth factors, tumor necrosis factors, epidermal growth factors, insulin-like growth factors. Complete factors, mimetics or active fragments thereof may be used.

The microcarriers may be inoculated with a second cell type and co-cultured with the anchorage-dependent postpartum cells. In one embodiment the two (or more) cell types may be adherent to an individual microcarrier in equal or un-equal proportions. The two or more cell types can be inoculated onto the microcarrier at the same time point or they may be inoculated at different times. The microcarriers can be treated in such a manner to preferentially adhere specific cell types onto specific regions of the microcarrier. In a further embodiment, the microcarrier with adherent single or multiple cell types can be co-cultured in a culture vessel with a second cell type cultured in suspension.

Second cell types may include, for example, epithelial cells (e.g., cells of oral mucosa, gastrointestinal tract, nasal epithelium, respiratory tract epithelium, vaginal epithelium, corneal epithelium), bone marrow cells, adipocytes, stem cells, keratinocytes, melanocytes, dermal fibroblasts, keratinocytes, vascular endothelial cells (e.g., aortic endothelial cells, coronary artery endothelial cells, pulmonary artery endothelial cells, iliac artery endothelial cells, microvascular endothelial cells, umbilical artery endothelial cells, umbilical vein endothelial cells, and endothelial progenitors (e.g., CD34+, CD34+/CD117+ cells)), myoblasts, myocytes, hepatocytes, smooth muscle cells, striated muscle cells, stromal cells, and other soft tissue cells or progenitor cells, chondrocytes, osteoblasts, islet cells, nerve cells including but not limited to neurons, astrocytes, Schwann cells, enteric glial cells, oligodendrocytes.

Also included are cells of cartilage tissue, meniscal tissue, ligament tissue, tendon tissue, intervertebral disc tissue, periodontal tissue, skin tissue, vascular tissue, muscle tissue, fascia tissue, periosteal tissue, ocular tissue, olfactory tissue, pericardial tissue, lung tissue, synovial tissue, nerve tissue, kidney tissue, bone marrow, urogenital tissue, intestinal tissue, liver tissue, pancreas tissue, spleen tissue, or adipose tissue.

Other embodiments and uses will be apparent to one skilled in the art in light of the present disclosures.

EXEMPLARY EMBODIMENTS

Example 1

Growth and Harvest of Umbilical Tissue-Derived Postpartum Cells on Microcarriers in Impeller Spinner Flask Bioreactors A goal of this work was to establish methods to seed, expand, and harvest human Umbilical Tissue-derived Cells (hUTCs) on microcarriers in impeller spinner flask bioreactors. The cells grown on microcarriers should exhibit similar growth kinetics and cell phenotype as cells cultured using static T-flask methods. As an initial step to determining if the cells cultured with these methods maintain their typical phenotype, an analysis of cell surface markers by flow cytometry was performed and compared with the cell surface markers expressed by (hUTCs) cultured in T-flasks. An additional goal of this work is to reduce the use of trypsin-EDTA (an animal derived product) in the method, thus reducing the risk of transmitting pathogens.

Materials and Methods:

Cells.

Cells from CBAT lot#050604B passage 8 cells were thawed and expanded in a T225 flask for one passage.

Microcarriers.

Cytodex 3® (GE Healthcare Life Sciences, cat. no, 17-0485) microcarrier beads were hydrated in PBS for at least 3 hours and autoclaved.

Spinner Flasks.

Spinner Flask with Internal Overhead Bearing Impeller Assembly, 100 ml and 250 ml (Bellco, Inc.).

Confluence.

Confluence is defined as approximately 90% of the microcarriers observed in a representative microscopy field to have greater than approximately 60% of their surface area covered with cells.

Passage.

Passage is defined as inoculating a spinner flask containing fresh microcarriers with an aliquot of confluent microcarriers obtained from a separate spinner flask culture.

Inoculation and Culture.

Cells were harvested from T225 flask by trypsin and 4.0E+06 cell aliquots were added to 330 mg of microcarrier beads in 100 ml impeller or glass rod spinner flask containing 40 ml media. Flasks were flushed with 5% $CO_2$ gas for 1 minute prior to incubation. The inoculum speed-frequency was 30 rpm for 2 minutes every 30 minutes for 8 hours. At eight hours media volume was increased to 100 ml and the spinner speed was set to 45-rpm continuous rotation and incubated at 37° C.

Passage.

Passage 1—(100 ml to 250 ml flask) Cells were cultured for eight days. All microcarriers from the 100 ml flask are collected and allowed to separate from media by gravity. Media was aspirated and microcarriers were re-suspended in 10 ml fresh media. After pipetting to ensure an even distribution, 5 ml of media with microcarriers were removed and delivered into a 250 ml spinner flask. Approximately 660 mg of fresh hydrated and autoclaved Cytodex® 3 microcarriers and media were also added to the flask. The media volume was increased to 200 ml and the flasks were flushed with 5%

$CO_2$ gas for 1 minute prior to incubation. The spinner speed was set to 45-rpm continuous rotation and incubated at 37° C. Remaining cells were harvested by trypsinization and counted by using a Guava® PCA instrument (Guava Technologies, Hayward, Calif.).

Passage 2—(250 ml to 250 ml flask) Cells were cultured for six days. All microcarriers from the 250 ml flask are collected and allowed to separate from media by gravity. Media was aspirated and microcarriers were re-suspended in 25 ml fresh media. After pipetting to ensure an even distribution, 5 ml of media with microcarriers were removed and delivered into a 250 ml spinner flask. Approximately 660 mg of fresh hydrated and autoclaved Cytodex® 3 microcarriers and media were also added to the flask. The media volume was increased to 200 ml and the flasks were flushed with 5% $CO_2$ gas for 1 minute prior to incubation. The spinner speed was set to 45-rpm continuous rotation and incubated at 37° C. Remaining cells were harvested by trypsinization and counted by using a Guava® PCA instrument.

Media Exchange.

Spinner flasks were removed from culture and the microcarriers were allowed to settle by gravity to the bottom of the flask. Approximately half the media volume was removed by aspiration and replaced with an equal volume of fresh media. The flasks were flushed with 5% $CO_2$ gas for 1 minute and returned to culture. Media exchange was performed on day 1, and day 4.

Viability Staining.

A 1 ml aliquot was removed from flask and microcarriers were allowed to settle by gravity. Media was removed by aspiration and replaced with 1 ml Live/Dead staining solution (Molecular Probes cat. no. L3224) and incubated for 15 minutes at 37° C. After incubation a 20-microliter aliquot was applied to a glass microscope slide and observed by fluorescent microscopy. Live cells stain green, dead cells stain red. Microscopic fields were manually analyzed to evaluate the distribution and ratio of live and dead cells adhered to the microcarriers. At least three microscopic fields were evaluated and the approximate percentage of viable cells was counted.

Cell Harvest.

Microcarriers were collected from the spinner flask, washed three times in PBS, and evenly distributed between two 50 ml conical tubes. Each tube was incubated with 25 ml trypsin for 10 minutes at 37° C. Tubes were brought to 50 ml volume with PBS and microcarriers were allowed to settle by gravity. Supernatant containing cells was collected by aspiration and transferred to 50 ml conical tubes pre-filled with 2.5 ml of FBS (yielding a 5% FBS solution to inactivate trypsin). This process was repeated four times with each fraction collected separately. All harvested cells were centrifuged, re-suspended in serum containing growth media, and cells were counted by using a Guava® PCA instrument.

Static T-Flask Culture.

An aliquot of cells harvested from the T225 flask are used to seed two T225 flasks and incubated for four days using methods stated in U.S. Publication No. 2005-0054098. The cells were harvested and analyzed by flow cytometry.

Flow Cytometry.

Cells harvested were analyzed by flow cytometry using a Becton-Dickinson FACSCalibur™ instrument (Becton Dickinson, San Jose, Calif.) to determine the cell surface marker profile. All antibodies purchased from BD PharMingen (San Diego, Calif.).

Results:

Cell Harvest.

Table 1 shows the harvest fractions, cell yields and viability per passage from Umbilical cell line 050604B expanded from passage nine to passage eleven on Cytodex 3® microcarriers in spinner flask cultures.

TABLE 1

| Passage | Fractions | Total Cells | Avg. Viability (%) |
|---|---|---|---|
| Inoculation | 4 | $2.85 \times 10^7$ | 99.7 +/− 0.19 |
| 1 | 8 | $9.34 \times 10^7$ | 99.2 +/− 2.65 |
| 2 | 4 | $8.80 \times 10^7$ | 94.4 +/− 1.92 |

Cell Kinetics.

Table 2 shows the growth kinetics from Umbilical cell line 050604B expanded from passage nine to passage eleven on Cytodex 3® microcarriers in spinner flask cultures. The table shows that the total doublings was 7.48, and the average hours per doubling was 69.53 (+/−17.52) hours.

TABLE 2

| Passage | Seeded | Yield | Days | Expansion | Doubling | Hours/Doubling |
|---|---|---|---|---|---|---|
|  |  | $2.00 \times 10^6$ | 0 | 1 |  |  |
| Inoculation | $2.00 \times 10^6$ | $2.85 \times 10^7$ | 8 | 14.3 | 3.83 | 50.09 |
| 1 | $2.85 \times 10^7$ | $9.34 \times 10^7$ | 6 | 3.28 | 1.71 | 84.12 |
| 2 | $2.30 \times 10^7$ | $8.80 \times 10^7$ | 6 | 3.83 | 1.94 | 74.39 |

Live/Dead Staining.

Analysis of the live/dead stained microcarrier aliquot shows the majority of the microcarrier surfaces covered with green stained (viable) cells with scant foci of red stained nuclei (dead). The cells exhibit morphology similar to the morphology of the cells cultured in static conditions.

Flow Cytometry Analysis.

Table 3 shows the results ("+ positive" or "− negative") for cell surface markers expressed by human Umbilical Tissue-derived Cells (hUTCs) harvested microcarrier beads in spinner flasks versus hUTCs harvested from culture in static T flasks. The table shows that the markers expressed by the cells produced by the two methods were consistent.

TABLE 3

Comparision of cell surface proteins expression by Umb 050604B cells expanded in static T flasks or on Cytodex 3 ® microcarriers in spinner flask systems and analyzed by flow cytometry.

| Cell Surface Marker | Static T Flasks | Cytodex 3 ® Microcarriers |
|---|---|---|
| CD 10 | (+) | (+) |
| CD 13 | (+) | (+) |
| CD 31 | (−) | (−) |
| CD 34 | (−) | (−) |
| CD 44 | (+) | (+) |
| CD 45 | (−) | (−) |
| CD 73 | (+) | (+) |
| CD 90 | (+) | (+) |

TABLE 3-continued

Comparision of cell surface proteins expression by Umb 050604B cells expanded in static T flasks or on Cytodex 3® microcarriers in spinner flask systems and analyzed by flow cytometry.

| Cell Surface Marker | Static T Flasks | Cytodex 3® Microcarriers |
|---|---|---|
| CD 117 | (−) | (−) |
| CD 141 | (−) | (−) |
| PDGFr-α | (+) | (+) |
| HLA-A, B, C | (+) | (+) |
| HLA-DR, DP, DQ | (−) | (−) |

Conclusions:

Human Umbilical Tissue-derived Cells (hUTCs) were cultured on Cytodex 3® microcarriers in impeller spinner flask bioreactors. The cells achieved 7.48 population doublings over twenty days and had an average population doubling time of 69 hours. Cell viability per passage ranged from 94.4% to 99.7%. Analysis for expression of thirteen cell surface markers on hUTCs cultured on microcarriers was consistent with the cell surface marker expression by hUTCs cultured in cell culture T flasks. This work provides initial evidence indicating microcarriers can be used to seed, expand, and harvest hUTCs in bioreactor systems.

Example 2

Growth of Expanded Human Umbilical Tissue-Derived Cells (hUTCs) on MGSA, HA, and PLGA Microcarriers in Spinner Flasks Microcarriers used in conjunction with aseptically closed systems can potentially produce commercial quantities of expanded Human Umbilical Tissue-derived Cells (hUTC). Aseptically closed systems reduce operator manipulation required to expand and maintain commercial cell products thus reducing operator error, contamination, and monitoring. Microcarriers provide a substantially larger surface area for cell attachment as compared to cell culture flasks, thereby producing higher cell yields.

The ability of hUTCs to attach to microcarriers made of synthetic resorbable biomaterials was investigated, including the ability to maintain viability in spinner flask culture, and to proliferate upon re-seeding into static culture. Expanded hUTCs were seeded onto microcarriers comprised of poly-(D,L-lactide-co-glycolide) (PLGA), sodium hyaluronate (HA), and poly(monostearoylglyceride co-succinic acid) (MGSA) materials. Commercially produced Cytodex 3® microcarriers were also used as a control in this example. The material with cells were cultured in spinner flasks for five days, harvested by trypsinization, and re-seeded into static cultures. The re-seeded cells expanded in static culture within four days demonstrating retention of their proliferative capacity. This example demonstrates the ability of synthetic biomaterials to be used as microcarriers for spinner flask culture.

Materials and Methods

TABLE 4

| Microcarriers | | | |
|---|---|---|---|
| Microcarrier | Manufacturer | Process Method | Avg. Size (microns) |
| PLGA (85/15) IV 0.75 | Alkermes (Willington, OH) | SCF | 149 |
| PLGA (50/50) IV 0.43 | Alkermes (Willington, OH) | SCF | 158 |
| MGSA I | Ethicon (Somerville, NJ) | SCF | 195 |
| MGSA II | Ethicon (Somerville, NJ) | Spinning Disk | 69 |
| MGSA III | Ethicon (Somerville, NJ) | Spinning Disk | 104 |
| HA | NovaMatrix (Drammen, Norway) | Torque Rheometer | 2000 |
| Cytodex 3 | Amersham Biosciences | NA | 175 |

Preparation of PLGA Microspheres.

PLGA Microspheres were Prepared by supercritical fluid process (SCF). The SCF unit was autoclaved or wiped with 70% ethanol and placed under the laminar flow hood. One gram of PLGA was poured into the chamber of SCF unit under the aseptic condition. The SCF unit was closed was moved into the regular fume hood. The unit was connected to an inlet tube with a 0.2-micron filter. Pressure and temperature were 300 bar and 35° C., respectively. The rotating speed of the blade was 250 rpm. The reaction was performed for 15 minutes. After completing the process, the SCF unit was disconnected with the tubes of the inlet and the outlet of $CO_2$ and moved into the laminar flow hood and the chamber was opened. The material produced was transferred to a grinder with liquid nitrogen and ground.

Preparation of MGSA Microspheres.

MGSA microspheres were prepared by supercritical fluid process. The SCF unit was autoclaved or wiped with 70% ethanol and placed under the laminar flow hood. Two grams of MGSA was poured into a chamber of SCF unit under the aseptic condition. The SCF unit was closed was moved into the regular fume hood. The unit was connected with an inlet tube with a 0.2-micron filter. Pressure and temperature were 150 bar and 35° C., respectively. The rotating speed of the blade was 250 rpm. The reaction was performed for 20 minutes. After completing the process, the SCF unit was disconnected with the tubes of the inlet and the outlet of $CO_2$ and moved into the laminar flow hood and the chamber was opened.

Sodium Hyaluronate Processing.

Five grams of sodium hyaluronate (Novamatrix, Pharm 80) was weighed out and the dry powder was placed in full size bowl of a Mixer Torque Rheometer (Caleva, U.K.). After 10 seconds of mixing in the torque rheometer at 50 rpm one milliliter of ethanol/water (50/50 v/v) solution was added manually (using a syringe) into the powder mixture. After the fluid addition, mixing continued for another 10 seconds at the same rate and another milliliter of ethanol/water solution was added. This pattern continued until 5 milliliters of solution was added. The wet mass was placed into the horizontal screw extruder attachment and a die containing 2.0 mm diameter holes equi-spaced on a single circular pattern was placed on the end of the extruder attachment. Screw speed was 50 rpm and a hand held ram was used to force the wet granulation into the screw. The formulation extruded into discrete strands that dried quickly. Extruded strands were cut manually with a straight edge razor blade into pellets of 2 mm in length.

Microcarrier Preparation.

Approximately 1 gram of each PLGA microcarrier was suspended in 25 ml Dulbecco's phosphate buffered saline (PBS) for one hour. PBS was removed by aspiration and materials were re-suspended in 25 ml of growth media for at least 30 minutes prior to inoculation.

Approximately 1 g of each MGSA microcarrier was suspended in 25 ml 70% ethanol for 30 minutes to wet the material. The ethanol was removed by aspiration and the MGSA was rinsed three times with PBS and re-suspended in 25 ml of growth media for at least 30 minutes prior to inoculation.

Sodium hyaluronate (260 mg) was sterilized in 25 ml 70% alcohol for 2 hours. The ethanol was removed by aspiration and then rinsed three times with PBS and resuspended in 25 ml of growth media for at least 30 minutes prior to inoculation.

The day before inoculation, 775 mg of Cytodex 3® microcarrier beads were hydrated in 40 ml PBS for at least 3 hours and autoclaved. On the day of inoculation, the PBS was removed by aspiration and the Cytodex 3® was re-suspended in growth media for at least 30 minutes prior to inoculation.

TABLE 5

Microcarrier quantity used.

| Microcarrier | Milligrams | No. cells Seeded |
| --- | --- | --- |
| PLGA (85/15) IV 0.75 | 700 | $9.00 \times 10^6$ |
| PLGA (50/50) IV 0.43 | 330 | $4.50 \times 10^6$ |
| MGSA I | 470 | $4.50 \times 10^6$ |
| MGSA II | 330 | $4.50 \times 10^6$ |
| MGSA III | 330 | $5.00 \times 10^6$ |
| HA | 261 | $4.50 \times 10^6$ |
| Cytodex 3 | 775 | $9.00 \times 10^6$ |

Inoculation and Culture.

The materials, cell type, growth media, spinner flask, inoculation and culture conditions, media exchange, viability staining and cell harvest methods used in Example 1 are used in this example.

Cell Harvest.

Due to large amounts of biomaterial debris in the MGSA spin disk (<75 μm), MGSA SCF, PLGA 50/50) and HA samples, and the potential for clogging the instrument, the harvested cells were not counted using the Guava® PCA. All harvested cells with debris were re-seeded into T225 flasks. Microcarrier harvest yields were back calculated from the re-seed harvest yields.

Results

Microcarrier Yield Calculations.

Microcarrier yields are calculated based on 39 hours population doubling time or 2.46 doubling in a four day period (historical data of hUTC growth kinetics in static conditions) The equation doublings=(Log 10(harvest)−Log 10(seeded))/Log 10(2) is used.

TABLE 5a

Final Cell Yields

| Microcarrier | Total Cells | Viability (%) |
| --- | --- | --- |
| PLGA (85/15) IV 0.75 | $1.49 \times 10^6$ | 92.3 |
| PLGA (50/50) IV 0.43 | $3.46 \times 10^6$ | NA |
| MGSA I | $8.51 \times 10^6$ | NA |
| MGSA II | $3.31 \times 10^3$ | NA |
| MGSA III | $2.30 \times 10^6$ | 94.3 |
| HA | $1.38 \times 10^5$ | NA |
| Cytodex 3 | $2.10 \times 10^7$ | 99.2 |

Harvest Cell Re-Seed.

Cells harvested from all materials (except Cytodex 3®) were re-seeded into T225 tissue culture flasks at approximately 5,000 cells per cm sq. The cells harvested from all materials proliferated upon re-seeding Expanded hUTCs were seeded onto PLGA, HA and MGSA materials, cultured in spinner flasks for five days, harvested by trypsinization, and re-seeded into static cultures. The cells that were harvested from the synthetic microcarriers were over 90% viable. The re-seeded cells expanded in static culture within four days demonstrating retention of their proliferative capacity. This example demonstrates the ability of synthetic biomaterials to be used as microcarriers for spinner flasks culture.

Example 3

Growth of Expanded Human Umbilical Tissue-Derived Cells (hUTCs) on Collagen Coated MGSA and PLGA Microcarriers in Spinner Flasks The ability of hUTCs to attach to materials made of synthetic resorbable biomaterials with a collagen coating was investigated, including the ability to maintain viability in spinner flask culture and to proliferate upon re-seeding into static culture. Expanded hUTCs were seeded onto collagen-coated or uncoated poly-(D,L-lactide-co-glycolide) (PLGA) and poly(monostearoylglyceride co-succinic acid) (MGSA) microcarriers. The microcarriers with cells were cultured in spinner flasks for five days, harvested by trypsinization, and re-seeded into static cultures.

Materials and Methods

TABLE 6

Microcarriers

| Microcarrier | Manufacturer | Process Method | Avg. Size (microns) |
| --- | --- | --- | --- |
| PLGA (50/50) IV 0.43 | Alkermes (Willington, OH) | SCF | 158 |
| MGSA I | Ethicon (Somerville, NJ) | SCF | 195 |

Microcarrier Preparation.

Microcarrier Wetting—Approximately 1 g each of MGSA and PLGA microcarriers were aseptically suspended in 25 ml 70% ethanol for 30 minutes to wet the microcarriers. The ethanol was removed by aspiration and the microcarriers were then rinsed three times with PBS and re-suspended 25 ml of in Dulbecco's phosphate buffered saline (PBS).

Collagen Coating.

Wetted microcarriers (PBS) were pelletized by centrifugation, the PBS removed by aspiration, and the microcarriers were re-suspended in a 2.9% collagen solution (Vitrogen 1000, Cohesion, Inc. Palo Alto, Calif.). The microcarriers were incubated in collagen for 30 minutes. The residual collagen was removed by aspiration and the collagen coated microparticles were washed three times with PBS.

TABLE 7

Microcarrier Quantities Used.

| Microcarrier | Milligrams | No. cells Seeded |
| --- | --- | --- |
| PLGA (50/50) uncoated | 260 | $3.50 \times 10^6$ |
| PLGA (50/50) coated | 260 | $3.50 \times 10^6$ |

TABLE 7-continued

Microcarrier Quantities Used.

| Microcarrier | Milligrams | No. cells Seeded |
|---|---|---|
| MGSA I uncoated | 330 | $3.50 \times 10^6$ |
| MGSA I coated | 330 | $3.50 \times 10^6$ |

Inoculation and Culture

The materials, cell type, growth media, spinner flask, inoculation and culture conditions, media exchange, viability staining and cell harvest methods used in Example 1 were used in this example.

Results

TABLE 7a

Cell Harvest.

| Microcarrier | Total Cells | Viability (%) |
|---|---|---|
| PLGA (50/50) uncoated | $1.20 \times 10^6$ | 98.6 |
| PLGA (50/50) coated | $1.15 \times 10^6$ | 97.6 |
| MGSA I uncoated | $1.82 \times 10^6$ | 99.0 |
| MGSA I coated | $2.39 \times 10^6$ | 97.8 |

Harvest Cell Re-Seed.

Cells harvested from the coated and uncoated MGSA and PLGA microcarriers were re-seeded into T225 at approximately 5,000 cells per cm sq. Four days after re-seeding the cells harvested from both materials proliferated to over 50% confluence.

Expanded human Umbilical Tissue-derived Cells (hUTCs) were seeded onto collagen coated PLGA and MGSA microcarrier, cultured in spinner flasks for five days, harvested by trypsinization, and re-seeded into static cultures. The cells that were harvested from the synthetic microcarriers were over 90% viable. The re-seed cells expanded in static culture within four days demonstrating retention of their proliferative capacity. This example demonstrates the ability of synthetic biomaterials to be used as microcarriers for spinner flasks culture.

Example 4

Growth of Expanded Human Umbilical Tissue-Derived Cells (hUTCs) on Gelatin Coated MGSA Microcarriers in Spinner Flasks The ability of hUTCs to attach to microcarriers made of synthetic resorbable biomaterials with a gelatin coating was investigated, including the ability to maintain viability in spinner flask culture and to proliferate upon re-seeding into static culture. Expanded hUTCs were seeded onto gelatin-coated or uncoated poly(monostearoylglyceride co-succinic acid) (MGSA) materials. Commercially produced Cytodex 3® microcarriers were also used as a control in this example. The microcarriers with cells were cultured in spinner flasks for five days, harvested by trypsinization, and re-seeded into static cultures.

Materials and Methods

TABLE 8

Microcarriers

| Microcarrier | Manufacturer | Process Method | Avg. Size (microns) |
|---|---|---|---|
| MGSA III | Ethicon (Somerville, NJ) | Spinning Disk | 104 |
| Cytodex 3 | Amersham Biosciences | NA | 175 |

Microcarrier Preparation.

See Example 1 for Cytodex 3® microcarrier preparation. See Example 2 for MGSA microcarrier wetting and preparation.

Gelatin Coating.

Uncoated MGSA in PBS were centrifuged, the PBS removed by aspiration, and re-suspended in 25 ml of a 2% gelatin solution. The microcarriers were incubated in gelatin for 30 minutes. The residual gelatin solution was removed by aspiration and the gelatin-coated microcarriers were washed three times with PBS and re-suspended in 25 ml PBS.

The day before inoculation, 775 mg Cytodex 3® microcarrier beads were hydrated in 40 ml PBS for at least 3 hours and autoclaved. On the day of inoculation, the PBS was removed by aspiration and the Cytodex 3® was re-suspended in growth media for at least 30 minutes prior to inoculation.

TABLE 9a

Microcarrier Quantities Used.

| Microcarrier | Milligrams | No. cells Seeded |
|---|---|---|
| MGSA III uncoated | 330 | $5.00 \times 10^6$ |
| MGSA III coated | 330 | $5.00 \times 10^6$ |
| Cytodex 3 | 775 | $9.00 \times 10^6$ |

Inoculation and Culture.

The microcarriers, cell type, growth media, spinner flask, inoculation and culture conditions, media exchange, viability staining and cell harvest methods used in Example 1 are used in this example with the following exceptions. The inoculum speed/frequency was 30 rpm for 2 minutes every 30 minutes for 8 hours. At eight hours media volume was increased to 100 ml for the MGSA and 250 ml for the Cytodex 3® and the spinner speed was set to 45-rpm continuous rotation and incubated at 37° C.

Media Exchange.

After three days of culture the flasks were removed from the stir plates and the microcarriers were allowed to settle. Approximately half (50 ml and 125 ml) the media volume was removed by aspiration and replaced with an equal volume of fresh growth media.

This method was used for the MGSA materials with the following exceptions; 50 ml conical tubes and 10 ml trypsin used.

All harvested cells were centrifuged, re-suspended in growth media, and cells were counted by using a Guava PCA instrument.

Results

TABLE 9b

Cell Harvest.

| Microcarrier | Total Cells | Viability (%) |
|---|---|---|
| MGSA III uncoated | $9.71 \times 10^5$ | 89.8 |
| MGSA III coated | $1.05 \times 10^6$ | 83.3 |
| Cytodex 3 | $4.50 \times 10^7$ | 98.6 |

Harvest Cell Re-Seed.

Cells harvested from the gelatin coated and uncoated MGSA materials were re-seeded into T225 flasks at approximately 5,000 cells per cm sq. Four days after re-seeding the harvested cells, the cells proliferated to over 50% confluence.

Expanded human Umbilical Tissue-derived Cells (hUTCs) were seeded onto MGSA materials, with a gelatin protein coating, cultured in spinner flasks for five days, harvested by trypsinization, and re-seeded into static cultures. The cells that were harvested from the synthetic microcarriers were over 80% viable. The re-seeded cells expanded in static culture within four days demonstrating retention of their proliferative capacity. This example demonstrates the ability of gelatin-coated synthetic biomaterials to be used as microcarriers for spinner flask culture.

Example 5

Feasibility of SoloHill Microcarrier-Based hUTC Cultures for Cell Production and Recovery Growth of expanded hUTCs was evaluated on microcarriers manufactured by SoloHill, Inc. SoloHill Engineering, Inc. (Ann Arbor, Mich.). The microcarrier beads are sold by SoloHill in their catalog, and will be referred to here as collagen-coated (catalog no. C104-1521), HILLEX® II (catalog no. H112-170), and pronectin-coated (ProNectin F, catalog no. PF104-1521).

For hUTC production in serum-containing media, collagen-coated, pronectin-coated and uncoated HILLEX® II microcarriers were evaluated for (1) cell attachment, (2) spreading, (3) growth, (4) efficiency of cell dissociation and (5) cell separation from microcarriers. Culture conditions were nearly identical to those used to grow hUTCs in gelatin coated T-225 flasks before seeding microcarrier cultures for experiments 1 through 5. Manual whole cell and cell release nuclei counts were used to calculate hUTC growth indices: cell number at culture initiation (seeding density (Ni)), cell harvest at a specified time point (Nh), time in culture expressed in hours (t), population doubling level (PDL), population doubling per 24 hours (r), and hours per population doubling (PDT).

In these studies uniform cell attachment to HILLEX® II and collagen-coated microcarriers occurred within 1 hr and 4 hrs respectively. Pronectin-coated microcarriers were eliminated from this example due to unsatisfactory attachment results. Similar to hUTC grown in gelatin-coated T-225 tissue culture flasks, spreading occurred soon after cell attachment to HILLEX® II and collagen-coated microcarriers. The measurement of growth, based on Nh and PDT values, were used to compare tissue cultures and microcarrier cultures; cells grown in T-225 tissue culture flasks were used to seed microcarrier culture experiments 1 through 5. For cells grown in T-flasks, Nh values were within a range of $3.5 \times 10^4/cm^2$ to $6.9 \times 10^4/cm^2$ and PDT values were in the range of 26-36. Using nearly identical cell culture conditions for the microcarrier culture feasibility studies, Nh/PDT ranges were basically identical to cells grown in T-flasks. The two outliers appear to be associated with the 92 hr±4 time point indicating, perhaps, that cells were in the stationary-death phase. Removal of cells from HILLEX® II and collagen-coated microcarriers and T-flasks resulted in robust, single cell suspensions. These preliminary results are promising and required for microcarrier culture scale-up of hUTCs. Separation of cells from HILLEX® II and collagen-coated microcarriers yielded recovery rates ranging from 72% to 146%.

Materials and Methods
Reagents:
All Studies
Tissue culture flasks—T-225 Corning, lot#13005020
2% Porcine Gelatin—Sigma Corp.
Culture Media—DMED low glucose, 15% FBS, 1 ppm BME, 1% penicillin/streptomycin
hUTC line: Umb 120304 P6
Bellco spinner flasks-100 to 250 working volume custom impeller by SoloHill
Engineering, Inc. Bellco straight blade impeller.

TABLE 10

SoloHill Engineering Microcarriers

| Microcarrier | Diameter (microns) | Surface Area ($cm^2$/gm) | # microcarriers/gm |
|---|---|---|---|
| HILLEX ® II | 160-180 | 515 | $5.7 \times 10^5$ |
| Collagen-coated | 124-212 | 360 | $4.6 \times 10^5$ |
| Pronectin-coated | 125-212 | 360 | $4.6 \times 10^5$ |

Spinner flask volume used for studies.
Rate was 225 $cm^2$/50 mls and 675 $cm^2$/150 mls as indicated in studies 1 through 5.
Abbreviations.
Ni=cell number at culture initiation (seeding density)
Nh=cell harvest at a specified time point
t=time in culture expressed in hours
PDL=population doubling level
r=population doubling per 24 hrs
PDT=hrs per population doubling
Microcarrier Preliminary Trypsinization Method
The flasks were transferred from the incubator to the biological safety hood allowing the HILLEX® II® or collagen-coated microcarriers allowed to settle by gravity. The media was removed from the settled microcarriers. The cell-laden microcarriers were thoroughly rinsed by adding DPBS at a rate of 2×-4× volume of the bead pack to the vessel being careful not to douse the microcarriers and dislodge the cells. The flask containing cell-laden microcarriers were then washed at 40-55 rpm, room temperature, for 15 minutes. The DPBS was removed and the wash step repeated. After removing the second rinse of DPBS, trypsin (0.05%) was added at a rate of 1×-2× volume of microcarrier pack. The flask containing cell-laden microcarriers was stirred at 40 rpm-55 rpm at room temperature for 15 minutes. The cells were removed from the microcarriers using microscopic observation in a 50-100 ml pipette. The microcarriers were moved up and down gently in the pipette to completely dislodge the cells. The microcarriers were allowed to settle by gravity and the cell containing supernatant was collected by pipette.

Process Development Steps for Sampling a Microcarrier Culture; Taking Samples for Testing and Modifying the Trypsinization Protocol.

The culture vessel was transferred from the incubator to the biological safety hood placing the vessel on a stir plate set at 60 rpm. With the culture in the stir mode, a 10 ml aliquot was obtained with a 15 ml pipette extended through one side-arm of the vessel into the mid-point of the culture and free of the impeller assembly. The aliquot was transferred to a 15 ml conical tube. (Note: for cells/ml, the bead pack is part of the 10 ml volume removed from the culture.). The microcarriers were allowed to settle by gravity and the media was removed by pipette. The cell-laden microcarriers were rinsed twice with 5 ml of DPBS. After removing the second rinse of DPBS, trypsin (0.05%) was added at a rate of 1×-2× volume of microcarrier pack and allowed to set for 10 minutes. The microcarriers were gently pipetted and dispensed repeatedly creating single cell suspension. The microcarriers were allowed to settle by gravity and the cell containing supernatant was collected by pipette, and the cells were counted.

Nuclei Release Method.

A 1-10 ml homogenous microcarrier culture sample, taken with the impeller rotating at 50-60 rpm, was transferred to a tube then centrifuged 200 g for 5 min before the supernatant was discarded. (Note: HILLEX® II did not require centrifugation). The pelleted microcarriers were suspended in 1 ml 0.1M citric acid (dissolved in water for the hypotonic effect) containing 0.1% w/v crystal violet. The contents of the tube were mixed well with a vibromixer (1 min) and then incubated for 1 hr at 37° C. Evaporation of the contents of the tube was avoided by using either a humidified incubator or by sealing the tube with plastic film. After incubation the contents of the tube were mixed again with the vibromixer before the released stained nuclei were counted with a haemocytometer. The microcarriers in the sample do not interfere with the counting. The samples can be stored for up to one week at 4° C. This method of determining the number of cells in the culture is most accurate when cultures are evenly suspended and when culture conditions have avoided aggregation of the microcarriers and cells.

Study 1 Experimental Design.

The object of this experiment was to define basic culture requirements for cell attachment and uniform distribution of cells among three types of SoloHill Microcarriers. (HILLEX® II (H), Collagen-coated (C) and Pronectin-coated (P)). Three microcarrier groups with two spinner flasks per group were set up. One flask in each group was initiated with constant stirring and the second flask in each group initiated with an intermittent stirring cycle (i). After 72 hours in culture, the contents of each culture flask was prepared for cell nuclei release counts.

Variables:

1) Microcarriers. HILLEX® 11 (H), Collagen-coated (C), or Pronectin-coated (PF) in each group 2) Stirring conditions within each group:
constant stirring at 50-60 rpm; or intermittent stirring 3 min on at 50-60 rpm and 30 min off for up to 24 hours before changing to constant stirring
3) Impeller. Custom impeller for the HILLEX® II microcarrier cultures, Bellco impeller for the two other microcarrier groups.

TABLE 11

Metrics per 225 cm² of microcarrier

| Microcarrier | Wt used (grams) | # microcarriers (appox) |
|---|---|---|
| HILLEX ® II | 0.44 | $2.5 \times 10^5$ |
| Collagen-coated | 0.63 | $2.9 \times 10^5$ |
| Pronectin-coated | 0.63 | $2.9 \times 10^5$ |

Constant culture conditions at initiation;
225 cm² total surface area per 50 ml media
$3.0 \times 10^6$ cells/225 cm²
pH 7.4
37° C./5% $CO_2$
CBAT serial hUTC line 120304 Passage 8

Results

Observations:

HILLEX® II cultures showed uniform cell distribution and single microcarriers confluent with cells both at constant stirring and intermittent on/off cycle. Collagen-coated microcarrier cultures showed uniform cell distribution and single microcarriers confluent with cell with constant stirring. Collagen-coated microcarrier intermittent cycle culture for the first 24 hours formed microcarriers aggregates, with cells growing around the aggregates dramatically decreasing the cell counts. Pronectin-coated microcarrier cultures were unsatisfactory using these culture conditions in both groups.

TABLE 12

Results of Cell Attachment on Microcarriers

| | Constant | | | Intermittent | | |
|---|---|---|---|---|---|---|
| | 1 hr | 4 hrs | 24 hrs | 1 hr | 4 hrs | 24 hrs |
| Cell attachment | H | H | H, C | H | H, PF, C | H, PF, C |
| Cell spreading | | H | H, C | | H, C | H, C |
| No attachment | PF | PF | PF | PF | | |
| No spreading | H, PF, C | PF, C | PF | H, PF, C | PF | PF |
| Partial attachment | C | C | | C | | |
| Uniform cell distribution | H | H | H, C | H | H | H |
| Microcarrier aggregation | | | | | | C |
| Cell aggregation | | PF | | | | PF |

TABLE 13

Results of Nuclei Counting After 74 hrs.
In Culture (i = intermittent)

| | cm2 | Ni | Nh | PDL | r | PDT |
|---|---|---|---|---|---|---|
| Collagen-coated | 225 | $3.00 \times 10^6$ | $1.66 \times 10^7$ | 2.47 | 0.80 | 30 |
| | 1 | $1.33 \times 10^4$ | $7.40 \times 10^4$ | | | |
| Collagen-coated i | 225 | $3.00 \times 10^6$ | $6.00 \times 10^6$ | 1.0 | 0.32 | 74 |
| | 1 | $1.33 \times 10^4$ | $2.70 \times 10^4$ | | | |
| HILLEX ® II | 225 | $3.00 \times 10^6$ | $1.24 \times 10^7$ | 2.05 | 0.66 | 36 |
| | 1 | $1.33 \times 10^4$ | $5.50 \times 10^4$ | | | |
| HILLEX ® II i | 225 | $3.00 \times 10^6$ | $1.26 \times 10^7$ | 2.06 | 0.67 | 35.8 |
| | 1 | $1.33 \times 10^4$ | $5.50 \times 10^4$ | | | |

As a result of this study, constant stirring for Collagen-coated and HILLEX® II microcarrier culture initiation will be used. The intermittent stirring cycle is not required for hUTC attachment and spreading in serum-containing media.

Study 2 Experimental Design.

To determine effects of seeding densities on the hUTC growth indices, two microcarrier groups with 3 flasks per group were initiated. Each of the 3 flasks within a group contained different seeding densities. Cell release nuclei count was used as a quantitative assay at one time point between days 3 and 4 in culture.

TABLE 14 hUTC seeding density per group:

| Group | $cm^2$ | Flask 1 | Flask 2 | Flask 3 |
|---|---|---|---|---|
| HILLEX ® II | 675 | $4.5 \times 10^6$ | $9.0 \times 10^6$ | $1.4 \times 10^7$ |
|  | 1 | $6.7 \times 10^3$ | $1.3 \times 10^4$ | $2.0 \times 10^4$ |
|  | Cells/microcarrier | 6 | 12 | 18 |
| Collagen-coated | 675 | $4.5 \times 10^6$ | $9.0 \times 10^6$ | $1.4 \times 10^7$ |
|  | 1 | $6.7 \times 10^3$ | $1.3 \times 10^4$ | $2.0 \times 10^4$ |
|  | Cells/microcarrier | 5 | 10 | 16 |

TABLE 15

Metrics per 675 $cm^2$ of microcarriers:

| Microcarrier | Wt used (grams) | # microcarriers (appox) |
|---|---|---|
| HILLEX ® II | 1.32 | $7.5 \times 10^5$ |
| Collagen-coated | 1.89 | $8.7 \times 10^5$ |

Constant culture conditions at initiation:

CBAT serial hUTC line 120304 Passage 9 constant stirring at 55-60 rpm

675 $cm^2$ (3×225 $cm^2$) surface area per 150 ml Hayflick media

37° C./5% $CO_2$ pH 7.4 time in culture one cell suspension pool for culture inoculation

Results of Cell Release Nuclei Counts and Cell Growth Indices after 88 Hrs in Culture TABLE 16a Count #1

|  | HILLEX ® II | | | Collagen-coated | | |
|---|---|---|---|---|---|---|
|  | Flask 1 | Flask 2 | Flask 3 | Flask 1 | Flask 2 | Flask 3 |
| Ni/675 $cm^2$ | $4.5 \times 10^6$ | $9.0 \times 10^6$ | $1.4 \times 10^7$ | $4.5 \times 10^6$ | $9.0 \times 10^6$ | $1.4 \times 10^7$ |
| Ni/$cm^2$ | $6.7 \times 10^3$ | $1.3 \times 10^4$ | $2.0 \times 10^4$ | $6.7 \times 10^3$ | $1.3 \times 10^4$ | $2.0 \times 10^4$ |
| Nh/675 $cm^2$ | $4.6 \times 10^7$ | $6.2 \times 10^7$ | $7.6 \times 10^7$ | $2.5 \times 10^7$ | $4.9 \times 10^7$ | $4.7 \times 10^7$ |
| Nh/$cm^2$ | $6.8 \times 10^4$ | $9.1 \times 10^4$ | $1.1 \times 10^5$ | $3.8 \times 10^4$ | $7.3 \times 10^4$ | $6.9 \times 10^4$ |
| PDL | 3.35 | 2.78 | 2.5 | 2.51 | 2.45 | 1.79 |
| r | 0.91 | 0.76 | 0.68 | 0.68 | 0.67 | 0.49 |
| PDT | 26 | 32 | 35 | 35 | 36 | 49 |

|  | HILLEX ® II | Collagen-coated |
|---|---|---|
| Ni/225 $cm^2$ | $3.0 \times 10^6$ | $3.0 \times 10^6$ |
| Ni/$cm^2$ | $1.3 \times 10^4$ | $1.3 \times 10^4$ |
| Nh/225 $cm^2$ | $1.0 \times 10^7$ | $8.1 \times 10^6$ |
| Nh/$cm^2$ | $4.4 \times 10^4$ | $3.6 \times 10^4$ |
| PDL | 1.7 | 1.5 |
| r | 0.57 | 0.47 |
| PDT | 42.1 | 51.1 |
| % viability | 98 | 97 |

TABLE 16b

Count #2

|  | HILLEX ® II | | | Collagen-coated | | |
|---|---|---|---|---|---|---|
|  | Flask 1 | Flask 2 | Flask 3 | Flask 1 | Flask 2 | Flask 3 |
| Ni/675 $cm^2$ | $4.5 \times 10^6$ | $9.0 \times 10^6$ | $1.4 \times 10^7$ | $4.5 \times 10^6$ | $9.0 \times 10^6$ | $1.4 \times 10^7$ |
| Ni/$cm^2$ | $6.7 \times 10^3$ | $1.3 \times 10^4$ | $2.0 \times 10^4$ | $6.7 \times 10^3$ | $1.3 \times 10^4$ | $2.0 \times 10^4$ |
| Nh/675 $cm^2$ | $3.9 \times 10^7$ | $5.6 \times 10^7$ | $6.7 \times 10^7$ | $1.7 \times 10^7$ | $4.0 \times 10^7$ | $4.7 \times 10^7$ |
| Nh/$cm^2$ | $5.7 \times 10^4$ | $8.3 \times 10^4$ | $1.0 \times 10^5$ | $2.4 \times 10^4$ | $6.0 \times 10^4$ | $6.9 \times 10^4$ |
| PDL | 3.1 | 2.64 | 2.3 | 1.9 | 2.19 | 1.79 |
| r | 0.85 | 0.72 | 0.63 | 0.52 | 0.6 | 0.49 |
| PDT | 28 | 33 | 38 | 46 | 40 | 49 |

Study 3 Experimental Design.

The purpose of this study was threefold; 1) determine the growth rate of hUTCs on HILLEX® II and collagen-coated microcarriers in culture for up to 96 hrs. At designated time points contents of the flasks in the example were prepared for cell nuclei release (CNR) counts. 2) Determine the efficiency of the trypsinization process in removing single cells from microcarriers and cell separation from microcarriers using a 74 micron mesh screen. Whole cell counts were used to measure results. 3) Results of whole cells counts and cell released nuclei counts were compared. Eight flasks were prepared; four in each group (H and C). Three flasks in each group were assayed by CNR at designated time points. One flask in each group was trypsinized and the cell suspension was filtered.

TABLE 17

Variables:

| Groups | $cm^2$ | Wt used (grams) | # microcarriers (appox) | impeller | Phenol Red |
|---|---|---|---|---|---|
| HILLEX ® II | 225 | 0.44 | $2.5 \times 10^5$ | custom | None |
| Collagen-coated | 225 | 0.64 | $2.9 \times 10^5$ | Bellco | included |

Cell Suspension Pool for Seeding Flasks
Cells suspended in Hayflick media with phenol Red
Cells suspended in Hayflick media without phenol Red
Constant Culture Conditions for Initiation
CBAT serial hUTC line 120304 Passage 10
Constant stirring at 55-60 RPM
225 $cm^2$ surface area per 50 mls of completed Hayflick media
37° C./5% $CO_2$
pH 7.4
Time points d2, d3 and d4 (expressed in hours post initiation)

TABLE 18

Results of growth curve expressed in cell release nuclei counts

| | HILLEX ® II | | | Collagen-coated | | |
|---|---|---|---|---|---|---|
| | 47 hrs | 73 hrs | 95 hrs | 47 hrs | 73 hrs | 95 hrs |
| Ni/225 $cm^2$ | | $3.0 \times 10^6$ | $3.0 \times 10^6$ | $3.0 \times 10^6$ | $3.0 \times 10^6$ | $3.0 \times 10^6$ |
| Ni/$cm^2$ | | $1.3 \times 10^4$ | $1.3 \times 10^4$ | $1.3 \times 10^4$ | $1.3 \times 10^4$ | $1.3 \times 10^4$ |
| Nh/225 $cm^2$ | | $1.4 \times 10^7$ | $2.2 \times 10^7$ | $7.3 \times 10^6$ | $1.7 \times 10^7$ | $1.5 \times 10^7$ |
| Nh/$cm^2$ | | $6.4 \times 10^4$ | $9.6 \times 10^4$ | $3.3 \times 10^4$ | $7.7 \times 10^4$ | $6.8 \times 10^4$ |
| PDL | | 2.2 | 2.8 | 1.3 | 2.5 | 2.3 |
| r | | 0.74 | 0.72 | 0.66 | 0.83 | 0.59 |
| PDT | | 32.6 | 33.6 | 36.4 | 29.8 | 40.7 |

Note:
insufficient cells to seed one HILLEX ® II flask. In the HILLEX ® II group the first time point (47 hrs) was not assayed.

TABLE 19

Results of trypsinization of T-225 $cm^2$ cell control at 73 hrs in culture expressed in whole cell counts

| | W/o Phenol Red | W/Phenol Red |
|---|---|---|
| Ni/675 $cm^2$ | $3.0 \times 10^6$ | $3.0 \times 10^6$ |
| Ni/$cm^2$ | $1.3 \times 10^4$ | $1.3 \times 10^4$ |
| Nh/675 $cm^2$ | $8.2 \times 10^6$ | $1.1 \times 10^7$ |
| Nh/$cm^2$ | $3.6 \times 10^4$ | $4.7 \times 10^4$ |
| PDL | 1.4 | 1.8 |
| r | 0.46 | 0.59 |
| PDT | 52.2 | 40.7 |

Study 4 Experimental Design.

Determine the efficiency of hUTC recovery following the trypsinization process and whole cell separation of hUTC from HILLEX® II and collagen-coated microcarriers. Four flasks were prepared; two flasks per group (H and C). One flask from each group trypsinized was assayed by whole cell counts; the second flask in each group was assayed by cell nuclei release counts.

TABLE 20

Variables:

| Groups | $cm^2$ | Wt used (grams) | # microcarriers (appox) | impeller | Phenol Red |
|---|---|---|---|---|---|
| HILLEX ® II | 675 | 1.32 | $7.5 \times 10^5$ | custom | None |
| Collagen-coated | 675 | 1.89 | $8.7 \times 10^5$ | Bellco | included |

Cell Suspension Pool for Seeding Flasks
Cells suspended in Hayflick media with Phenol Red
Cells suspended in Hayflick media without Phenol Red
Time in Culture; HILLEX® II cultures 96 hrs, collagen 72 hrs
Constant Culture Conditions for Initiation
CBAT serial hUTC line 120304 Passage 8
$9.0 \times 10^6$ cells per 675 $cm^2$
constant stirring @ 55-60 rpm
675 $cm^2$ per 150 mls Hayflick media
37° C./5% $CO_2$
pH 7.4

TABLE 21

Results of whole cell counts and cell release nuclei counts (NRC) from collagen at 72 hrs

| | Pre-filtration | | Post filtration (74 micron) | |
|---|---|---|---|---|
| | Whole cell | NCR | Whole cell | Recovery (%) |
| Ni/675 $cm^2$ | $9.0 \times 10^6$ | | | |
| Ni/$cm^2$ | $1.3 \times 10^4$ | | | |
| Nh/675 $cm^2$ | $2.5 \times 10^7$ | $2.2 \times 10^7$ | $2.2 \times 10^7$ | 88 |
| Nh/$cm^2$ | $3.7 \times 10^4$ | $3.2 \times 10^4$ | $3.2 \times 10^4$ | |

TABLE 21-continued

Results of whole cell counts and cell release
nuclei counts (NRC) from collagen at 72 hrs

|  | Pre-filtration | | Post filtration (74 micron) | |
| --- | --- | --- | --- | --- |
|  | Whole cell | NCR | Whole cell | Recovery (%) |
| PDL | 1.47 | 1.28 | | |
| r | 0.49 | 0.43 | | |
| PDT | 49 | 56 | | |

TABLE 22

Results of whole cell counts and cell release nuclei
counts (NRC) from HILLEX ® II at 96 hrs

|  | Pre-filtration | | Post filtration (74 micron) | |
| --- | --- | --- | --- | --- |
|  | Whole cell | NCR | Whole cell | Recovery (%) |
| Ni/675 cm$^2$ | $9.0 \times 10^6$ | | | |
| Ni/cm$^2$ | $1.3 \times 10^4$ | | | |
| Nh/675 cm$^2$ | $1.3 \times 10^7$ | $4.1 \times 10^7$ | $1.9 \times 10^7$ | 146 |
| Nh/cm$^2$ | $1.9 \times 10^4$ | $6.0 \times 10^4$ | $2.8 \times 10^4$ | |
| PDL | | | | |
| r | | | | |
| PDT | | | | |

Notes:
at 96 hrs HILLEX ® II CBAT cultures were highly confluent as indicated by the high NRC counts. However, following trypsinization there was much viscous material indicating a massive dead cell population as indicated by the low whole cell counts. Cells that escaped the viscous material were single cells with a viability of 82%.

Study 5 Experimental Design.

The efficiency of CBAT trypsinization and whole cell separation from collagen and HILLEX® II microcarriers will be evaluated. Eight culture flasks were prepared; four identical flasks per group (H and C). One flask from each of the two groups was trypsinized and cells filtered through a 74 micron mesh filter; the second flask from each group was assayed by cell release nuclei counts. Whole cell counts and CRN counts were compared for consistency. Two time points were evaluated. Cultures were seeded at the lower seeding density ($6.66 \times 10^3$/cm$^2$).

TABLE 23

Variables:

| Groups | cm$^2$ | Wt used (grams) | # microcarriers (appox) | impeller |
| --- | --- | --- | --- | --- |
| HILLEX ® II | 225 | 0.44 | $2.5 \times 10^5$ | custom |
| Collagen-coated | 225 | 0.63 | $2.9 \times 10^5$ | Bellco |

Constant Culture Conditions for Initiation
CBAT serial hUTC line 120304 Passage 9
one cell suspension pool for inoculation
constant stirring @ 55-60 rpm
225 cm$^2$ per 50 mls Hayflick medium with phenol red
37° C./5% $CO_2$
pH 7.4
time in culture; 69 and 92 hrs
$150 \times 10^4$ cells per 225 cm$^2$

TABLE 24

Results of whole cell counts and cell release
nuclei counts (NRC) from collagen at 69 hrs

|  | Pre-filtration | | Post filtration (74 micron) | |
| --- | --- | --- | --- | --- |
|  | Whole cell | NCR | Whole cell | Recovery (%) |
| Ni/675 cm$^2$ | $1.5 \times 10^6$ | | | |
| Ni/cm$^2$ | $6.7 \times 10^3$ | | | |
| Nh/675 cm$^2$ | $8.9 \times 10^6$ | $9.8 \times 10^6$ | $7.0 \times 10^6$ | 79 |
| Nh/cm$^2$ | $4.0 \times 10^4$ | $4.3 \times 10^4$ | $3.1 \times 10^4$ | |
| PDL | 2.57 | 2.7 | | |
| r | 0.89 | 0.94 | | |
| PDT | 27 | 26 | | |

TABLE 25

Results of whole cell counts and cell release nuclei
counts (NRC) from HILLEX ® II at 69 hrs

|  | Pre-filtration | | Post filtration (74 micron) | |
| --- | --- | --- | --- | --- |
|  | Whole cell | NCR | Whole cell | Recovery (%) |
| Ni/675 cm$^2$ | $1.5 \times 10^6$ | | | |
| Ni/cm$^2$ | $6.7 \times 10^3$ | | | |
| Nh/675 cm$^2$ | $8.9 \times 10^6$ | $8.9 \times 10^6$ | $6.4 \times 10^6$ | 72 |
| Nh/cm$^2$ | $4.0 \times 10^4$ | $4.0 \times 10^4$ | $2.8 \times 10^4$ | |
| PDL | 2.56 | 2.57 | | |
| r | 0.89 | 0.89 | | |
| PDT | 27 | 27 | | |

Note:
the 25 ml post-filtration cell suspension from the HILLEX ® II culture was transferred to a T-225 flask. This culture represents all the cells from the HILLEX ® II culture at 69 hrs. The next day the cells were be trypsinized and counted. The assumption was made that the viable cells will attach and spread before replicating therefore, the cells rescued at 24 hrs will equal the cells plated from the HILLEX ® II culture.

TABLE 26

Results of the T-225 culture at 24 hrs seeded with
the hUTC from the HILLEX ® II culture

|  | Whole cell |
| --- | --- |
| Nh/225 cm$^2$ | $1.07 \times 10^7$ |
| Nh/cm$^2$ | $4.75 \times 10^4$ |

TABLE 27

Results of whole cell counts and cell
release nuclei counts A(NRC) at 92 hrs

|  | Collagen-coated | | HILLEX ® II | T-225 control |
| --- | --- | --- | --- | --- |
|  | Whole cell | NRC | NRC | Whole cell |
| Ni/225 cm$^2$ | $1.5 \times 10^6$ | | $1.5 \times 10^6$ | $1.5 \times 10^6$ |
| Ni/cm$^2$ | $6.7 \times 10^3$ | | $6.7 \times 10^3$ | $6.7 \times 10^3$ |
| Nh/225 cm$^2$ | $1.2 \times 10^7$ | $1.2 \times 10^7$ | $1.4 \times 10^7$ | $1.2 \times 10^7$ |
| Nh/cm$^2$ | $5.2 \times 10^4$ | $5.4 \times 10^4$ | $6.3 \times 10^4$ | $5.2 \times 10^4$ |
| PDL | 3.0 | 3.0 | 3.2 | 3.0 |
| r | 0.77 | 0.78 | 0.85 | 0.78 |
| PDT | 31.2 | 30.8 | 28.2 | 30.8 |

In these studies, uniform cell attachment to HILLEX® II and collagen-coated microcarriers occurred within 1 hr and 4 hrs respectively. Pronectin was eliminated from the example due to unsatisfactory attachment results. Similar to hUTC grown in gelatin-coated T-225 tissue culture flasks, spreading occurred soon after cell attachment to HILLEX® II and collagen-coated microcarriers. The measure of growth based on Nh and PDT values was used to compare tissue cultures and microcarrier cultures; cells grown in T-225 tissue culture flasks were used to seed microcarrier culture experiments 1 through 5. For cells grown in T-flasks, Nh values were within a range of $3.5\times10^4/cm^2$ to $6.9\times10^4/cm^2$ and PDT values were in the range of 26-36. Using nearly identical cell culture conditions for the microcarrier culture feasibility studies, Nh/PDT ranges were identical to cells grown in T-flasks. The two outliers appear to be associated with the 92 hrs±4 time point indicating, that perhaps cells were in the stationary-death phase. Removal of cells from HILLEX® II, collagen-coated microcarriers, and T-flasks resulted in robust, single cell suspensions. These results were promising and required for microcarrier culture scale-up of hUTCs. Separation of cells from HILLEX® II and collagen-coated microcarriers yielded recovery rates ranging from 72% to 146%.

Example 6

Growth of Expanded Human Umbilical Tissue-Derived Cells (hUTCs) on Cytodex 3® Microcarriers in Wave Bioreactor Systems Microcarriers used in conjunction with aseptically closed systems can potentially produce commercial quantities of expanded human umbilical tissue derived cells (hUTCs). Aseptically closed systems reduce operator manipulation required to expand and maintain commercial cell products thus reducing operator error, contamination, and monitoring. Microcarriers provide a substantially larger surface area for cell attachment as compared to cell culture flasks, thereby producing higher cell yields.

The current work provides initial methods for the expansion of hUTCs on microcarriers in an aseptically closed Wave Biotech, Inc. bioreactor system (Wave Biotech LLC, Somerset, N.J.). Using the below methods, hUTCs were initially seeded onto Cytodex 3® microcarriers in a 250 ml spinner flask system and cultured for five days. The microcarriers with attached cells were then transferred into a Wave system containing additional media and cell free microcarriers and cultured for seven days. The transfer or passage of cells from the 250 ml spinner flask to the 1 L Wave system was achieved without the use of trypsin. This eliminates an animal derived product from the cell expansion process. The hUTCs achieved 3.02 population doubling in 12 days in the Wave system. At harvest, the cells were evenly distributed on all microcarriers sampled.

Materials and Methods
Cells.
hUTC line 120304 Passage 9
Media.
Dulbecco's Modified Eagles Media (DMEM)-low glucose, 15% fetal bovine serum (FBS), penicillin/streptomycin (P/S), Betamercaptoethanol (BME)
250 ml Spinner Flask Culture
Microcarriers.
Cytodex 3® (GE Healthcare Life Sciences, cat. no, 17-0485) microcarrier beads were hydrated in PBS for at least 3 hours and autoclaved.
Spinner Flasks.
Spinner Flask with Internal Overhead Bearing Impeller Assembly, 250 ml (Bellco, Inc.)
Inoculation and Culture.
Cells at approximately 70% confluence were harvested from T225 flask by trypsin and $9.0\times10^6$ cell aliquots were added to 660 mg of microcarrier beads in 250 ml impeller spinner flask containing 80 ml media. Flasks were flushed with 5% $CO_2$ gas for 1 minute prior to incubation. The inoculum speed-frequency was 30 rpm for 2 minutes every 30 minutes for 8 hours. At eight hours, media volume was increased to 250 ml and the spinner speed was set to 45-rpm continuous rotation and incubated at 37° C.

Wave Bioreactor
Microcarrier Transfer and Equipment Loading.
Microcarriers with attached cells were harvested from the 250 ml spinner flask and re-suspended in 50 ml media. This solution was added to a 2 L Wave bioreactor bag (cat. no. CELLBAG2L/S-NU) containing 1 L media and 2.4 g hydrated and autoclaved cell free Cytodex 3® microcarriers. The Wave bag was loaded onto a Wave Biotech 2/10EH system. to the Wave bag was inflated per manufacturers specs using 5% $CO_2$-atmospheric. The system's heating pad was set to 37° C.
Inoculation Phase.
The 2/10EH system was set at a 20 angle and a rocking speed of 6 rpm for approximately 16 hours (overnight).
Expansion Phase.
The 2/10EH system was set at a 5° angle and a rocking speed of 10 rpm for seven days.
Viability Staining.
A 1 ml aliquot of media and microcarriers were transferred to a 15 ml conical tube and the microcarriers were allowed to separate by gravity. Media was removed by aspiration, replaced with 1 ml Live/Dead staining solution (Molecular Probes cat. no. L3224), and incubated for 15 minutes at 37° C. After incubation, a 20 microliter aliquot of the cell suspension was applied to a glass microscope slide and observed by fluorescent microscopy. Live cells stain green and dead cells stain red. Microscopic fields were manually analyzed to evaluate the distribution of viable cells adhered to the microcarriers. At least three microscopic fields were evaluated and the approximate percentage of viable cells was counted.
Cell Harvest.
Microcarriers were collected from the wave bag into four 250 ml conical tubes, washed three times in PBS, and combined into one 250 ml conical tube. Microcarriers were incubated with 25 ml trypsin for 10 minutes at 37° C. with agitation. Tubes were brought to 200 ml volume with PBS and microcarriers were allowed to settle by gravity. Supernatant containing cells was collected by aspiration and transferred to 250 ml conical tubes pre-filled with 10 ml of FBS (yielding a 5% FBS solution to inactivate trypsin). This process was repeated two times with all fractions combined. All harvested cells were centrifuged, re-suspended in serum containing growth media, and cells were counted by using a Guava® PCA instrument.

TABLE 28

Results:

| Passage | Seeded | Yield | Days | Expansion | Doubling | Hours/Doubling |
|---|---|---|---|---|---|---|
|  |  | $9.00\times10^6$ | 0 | 1 |  |  |
| 9 | $9.00\times10^6$ | $7.29\times10^7$ | 12 | 8.1 | 3.02 | 95.43 |

The transfer of cells from the 250 ml spinner flask to the Wave system was achieved without the use of trypsin. This eliminates an animal derived product from the cell expansion process. The hUTCs achieved 3.02 population doubling in 12 days in the Wave system. At harvest, the cells were evenly distributed on all microcarriers sampled. This method demonstrates the ability of expanded human umbilical tissue-derived cells to be seeded, expanded, and harvested from microcarriers cultured in Wave Biotech bioreactor systems.

Example 7

Growth of Expanded Human Umbilical Tissue-Derived Cells (hUTC) on Cytodex 3® Microcarriers in a Three Liter Bioreactor Systems Microcarriers used in conjunction with aseptically closed systems can potentially produce commercial quantities of expanded human umbilical tissue-derived cells (hUTC). Aseptically closed systems reduce operator manipulation required to expand and maintain commercial cell products thus reducing operator error, contamination, and monitoring. Microcarriers provide a substantially larger surface area for cell attachment as compared to cell culture flasks, thereby producing higher cell yields.

The current work provides initial methods for the expansion of hUTCs on microcarriers in an aseptically closed three-liter bioreactor system with impeller agitation. The hUTCs achieved 2.88 population doublings in this system. Glucose consumption and lactate production in the bioreactor over time was indicative of metabolically active cells. At harvest, the cells present appeared to be evenly distributed on the microcarriers sampled. The cells harvested from the bioreactor on re-seeding into static culture conditions expanded to confluence demonstrating retention of the cells proliferative capacity. This method demonstrates the ability of expanded human umbilical tissue-derived cells to be seeded, expanded, and harvested from microcarriers cultured in an aseptically closed three-liter bioreactor system with impeller agitation.

Using these methods, hUTCs were initially seeded onto Cytodex 3® microcarriers in a 250 ml spinner flask system and cultured for five days. The microcarriers with attached cells were then transferred into the bioreactor system containing 1 L of media and additional cell free microcarriers and cultured for seven days. At day seven an additional 2 L of media and additional cell free microcarriers were added to the bioreactor system and cultured for ten days.

Materials and Methods

Cells.
  hUTC line Umb 120304, passage 9

Media.
  Dulbecco's Modified Eagles Media (DMEM)-low glucose, 15% fetal bovine serum (FBS), penicillin/streptomycin (P/S), Betamercaptoethanol (BME)

250 ml Spinner Flask

Microcarriers.
  Cytodex 3® (GE Healthcare Life Sciences, cat. no, 17-0485) microcarrier beads were hydrated in PBS for at least 3 hours and autoclaved.

Spinner Flasks.
  Spinner Flask with Internal Overhead Bearing Impeller Assembly, 250 ml (Bellco, Inc.)

Inoculation and Culture.
  Cells at approximately 70% confluence were harvested from T225 flask by trypsin and 9.0E+06 cell aliquots were added to 660 mg of microcarrier beads in 250 ml impeller spinner flask containing 80 ml media. Flasks were flushed with 5% $CO_2$ gas for 1 minute prior to incubation. The inoculum speed-frequency was 30 rpm for 2 minutes every 30 minutes for 8 hours. At eight hours, media volume was increased to 250 ml and the spinner speed was set to 45-rpm continuous rotation and incubated at 37° C.

Bioreactor Equipment.
  A three liter closed bioreactor system with impeller agitation was used. The system parameters (pH, oxygen tension, temp, impeller rpm) were controlled with a BioStat B-DCU (B. Braun International).

Pre-Bioreactor Harvest.
  Microcarriers with attached cells were harvested from the 250 ml spinner flask and re-suspended in 30 ml media. A 5 ml aliquot of the suspension (containing approximately 100 mg or ⅙ of the total microcarriers) was removed. The cells from this aliquot were harvested using methods listed below.

Microcarrier Transfer—250 ml to 1 L
  The remaining 500 mg of microcarriers with attached cells harvested from the 250 ml spinner flask were re-suspended in 50 ml media. This solution was added to a 2 L Wave bioreactor bag (cat. no. CELLBAG2L/S-NU) containing 1 L media and 2.6 g hydrated and autoclaved cell-free Cytodex 3® microcarriers. The Wave bag was then sterile welded onto an inlet port to the bioreactor and the contents transferred by gravity drain. The impeller was then initiated and maintained at 45 rpm.

Microcarrier Transfer—1 L to 3 L
  The wave bag methods listed above were used with the wave bag containing 2 L media and 6 grams of empty microcarriers.

Sampling.
  A 1 ml aliquot of media and microcarriers were transferred to a 15 ml conical tube and the microcarriers were allowed to separate by gravity. Media was aspirated and replaced with 1 ml Live/Dead staining solution (Molecular Probes cat. no. L3224) and incubated for 15 minutes at 37° C. After incubation, a 20 microliter aliquot of the cell suspension was applied to a glass microscope slide and observed by fluorescent microscopy. Live cells stain green and dead cells stain red. Microscopic fields were manually analyzed to evaluate the distribution of viable cells adhered to the microcarriers. At least three microscopic fields were evaluated and the approximate percentage of viable cells was counted.

Glucose Assay.
  Samples of media were obtained from the culture and assayed for glucose and lactate content.

Harvest.
  A 5 L Labtainer BioProcess Container (Hyclone, cat. no. SH30640.01) was sterile welded onto an outlet port attached to the bioreactor. The container was positioned below the bioreactor and the contents were transferred by gravity drain. The contents of the container were then aseptically transferred into (3) 750 $cm^2$ roller bottles (Corning LifeSciences, Corning, N.Y.). Cell adherent microcarriers were washed with PBS and combined into a single roller bottle. Microcarriers were incubated with 100 ml trypsin for 10 minutes at 37° C. with agitation. Tubes were brought to 1 L volume with PBS and microcarriers were allowed to settle by gravity. Supernatant containing cells was collected by aspiration and transferred to four 250 ml conical tubes each pre-filled with 10 ml of FBS (yielding a 5% FBS solution to inactivate trypsin). All harvested cells were centrifuged, re-suspended in serum containing growth media, and cells were counted by using a Guava® PCA instrument.

Results

Media Addition.
  On day 15, 500 ml of media were added to the system due to low glucose readings.

3 L Bioreactor Cell Kinetics.
  Cell number at seeding calculated from the cell harvest of ⅕ of the 250 ml spinner flask total microcarrier volume.

TABLE 29

| | | 250 ml pre-3 L Bioreactor | | | | |
|---|---|---|---|---|---|---|
| Passage | Seeded | Yield | Days | Expansion | Doubling | Hours/Doubling |
| 9 | 1.10 × 10$^7$ | 1.10 × 10$^7$<br>8.10 × 10$^7$ | 0<br>17 | 1<br>7.36 | 2.88 | 141.65 |

Observations and RPM Adjustments.

On day three (total volume 1 L) microcarrier settling was noted at the bottom of the bioreactor vessel. The impeller speed was increased to 60 rpm. On day 10 (three days after adjusting total volume to 3 L) microcarrier settling was again noted. The impeller speed was again increased to 85 rpm. On the day of harvest (day 17), microcarrier settling was again noted at the bottom of the bioreactor vessel.

Harvest Cell Re-Seed.

Cells harvested from the bioreactor were re-seed at 5,000 cells per cm sq in a T75 flask and expanded to confluence demonstrating the retention of their proliferative potential.

The transfer of cells from the 250 ml spinner flask to the Bioreactor system and the scale-up from 1 L to 3 L at day seven was achieved without the use of trypsin. This eliminates an animal derived product from the cell expansion process. The hUTCs achieved 2.88 population doublings in this system. Glucose consumption and lactate production in the bioreactor over time was indicative of metabolically active cells. At harvest, the cells present appeared to be evenly distributed on the microcarriers sampled. The cells harvested from the bioreactor on re-seeding into static culture conditions expanded to confluence demonstrating retention of the cells proliferative capacity. This method demonstrates the ability of expanded human umbilical tissue derived cells to be seeded, expanded, and harvested from microcarriers cultured in an aseptically closed three-liter bioreactor system with impeller agitation.

Example 8

Expansion of hUTC in Reduced Fetal Bovine Serum Growth Medium

The goal of this study was to compare the growth kinetics and cell surface markers of continuously cultured expanded human umbilical tissue derived cells (hUTC) in standard growth medium, which contains 15% fetal bovine serum (FBS), or a reduced serum growth medium, containing 7.5% FBS. Production of hUTC cell therapy products in reduced serum media will increase product safety by decreasing the use of animal derived products. The use of reduced serum media will also reduce production costs and reduce foaming potential in gas-sparged bioreactors.

Data generated in microplate format proliferation assays of hUTC in standard growth media and reduced serum media indicated that hUTC actively proliferated in reduced serum media. As a result of these proliferation data, the growth kinetics and surface protein expression phenotype of hUTC were assessed over multiple passages in tissue culture flask conditions. Cryopreserved hUTC isolate 120304 was thawed and used to immediately inoculate T75 flasks containing standard or reduced serum media and were continuously cultured over multiple passages. The cell surface protein expression of the harvested cells from each media was analyzed by flow cytometry. Additionally, cryopreserved hUTC isolate 120304 was thawed and used to immediately inoculate spinner flasks containing HILLEX® II microcarriers containing standard or reduced serum media and were continuously cultured over multiple passages.

Cryopreserved hUTC isolate 120304 was thawed and expanded in replicate T75 flasks with reduced serum growth media for eleven passages. The hours per population doubling for each replicate T75 flask was consistent from passage to passage, indicating stable logarithmic growth. Statistical analysis by one-way ANOVA of all hours per population doubling data points show no significant difference in hUTC growth kinetics for all data points (p=0.821), as compared to the standard growth medium control. The cell surface protein expression of hUTC expanded in reduced serum media was consistent with hUTCs expanded in standard growth media.

Additionally, cryopreserved hUTC isolate 120304 was thawed and expanded on Hillex II microcarrier containing spinner flasks with reduced serum growth media for three passages. The hours per population doubling for each spinner flask was consistent from passage to passage, indicating stable logarithmic growth. Statistical analysis by two-sample T-test of the average hours per population doubling show no significant difference the hUTC growth kinetics between the two medias tested. (p=0.424).

These data demonstrated the ability of hUTC to be expanded in static T flask or microcarrier culture systems with reduce serum media over multiple passages in a stable, consistent manner, while maintaining the phenotypic cell surface protein expression. The goal of this study was to compare the growth kinetics and cell surface markers of continuously cultured expanded human umbilical tissue derived cells (hUTC) in standard growth medium, which contains 15% fetal bovine serum (FBS) and a reduced serum growth medium containing 7.5% FBS. Production of hUTC cell therapy products in a reduced serum medium will increase product safety by decreasing the use of animal derived products. Additionally, the use of a reduced serum medium will increase production efficiency by lowering the cost of materials and reducing foam potential during culture in gas-sparged bioreactors.

The proliferation of hUTC in a microplate format assay indicated the potential for continuous culture in reduced serum conditions. This assay initially included serial dilutions of FBS ranging from 15% to 0% in standard basal growth medium and in an alternative reduced serum basal medium, in a 96-well format. After culturing for 96 hours, it was found that hUTC proliferation for both basal media was best in the 15%, 7.5% and 3.75% FBS containing media. As a result, a second microplate assay was established in a 24-well format, using only the three lead FBS concentrations for both basal medium types. Based on the observed proliferation in the 24-well format, a comparison of hUTC growth kinetics was initiated for standard growth medium with 15% FBS and the alternative basal growth medium with 7.5% FBS.

Cryopreserved hUTC isolate 120304 was thawed and used to immediately inoculate T75 flasks containing standard or reduced serum media and were continuously cultured over multiple passages. The cell surface protein expression of the harvested cells from each media was analyzed by flow cytometry. Additionally, cryopreserved hUTC isolate 120304 was thawed and used to immediately inoculate spinner flasks containing Hillex II microcarriers containing standard or reduced serum media and were continuously cultured over multiple passages.

Materials and Methods

Cells.

Cryopreserved expanded human umbilical cord tissue cells (hUTC) isolate 12034 population doubling (PD) 12.

Growth Media (Hayflick).

Dulbecco's Modified Eagles Media (DMEM)-low glucose (Gibco; Grand Island, N.Y.), 15% fetal bovine serum (FBS) (HyClone; Logan, Utah), penicillin/streptomycin (P/S) (Gibco; Grand Island, N.Y.), Betamercaptoethanol (BME) (Sigma; St. Louis, Mo.)

Reduced Serum Media (Adv. DMEM/F12)

Advanced DMEM/F12 (Gibco; Grand Island, N.Y.), 7.5% fetal bovine serum (FBS), penicillin/streptomycin (P/S), 4.0 mM GlutaMAX™ (Gibco; Grand Island, N.Y.), Multi-Well Microplates.

Tissue culture 96-well and 24-well microplates (Corning, Inc.; Corning, N.Y.) coated with gelatin (Sigma; St. Louis, Mo.).

Tissue Culture Flasks.

T75 flasks (Corning Inc.; Corning, N.Y.) coated with gelatin.

Microcarriers.

HILLEX® II microcarriers (Solo Hill; Ann Arbor, Mich.) were hydrated in DI water for at least 30 minutes and autoclaved. HILLEX® II microcarriers were used at a concentration of 12 g/L.

Spinner Flasks.

100 ml and 500 ml single-use, disposable spinner flasks (Corning, Inc.; Corning, N.Y.) were used as culture vessels.

Inoculation and Culture in 96-Well Microplates.

Cryopreserved vials of hUTC were thawed, washed and resuspended in growth media. Growth medium was prepared using both Hayflick and Adv. DMEM/F12, supplemented with 15%, 7.5%, 3.75%, 1.88%, 0.94% or 0% FBS. $5.00 \times 10^3$ hUTC per well were added to two wells per condition. Each well contained 250 µl growth medium. The plate was cultured in 5% $CO_2$, 37° C. tissue culture incubators for 96 hours.

Harvest and Counting of Cells from 96-Well Microplates.

The cell containing 96-well microplate was removed from incubation and media removed by aseptic aspiration. The cells were washed with 100 µl PBS per well; PBS was removed by aseptic aspiration and 75 µl TrypLE™ Select (Gibco; Grand Island, N.Y.) was added. The cells were incubated for 5 minutes at 37° C., after which, the plate was lightly tapped to dislodge the cells. 75 µl of appropriate medium was added to each well. An addition 50 µl of counting reagent was added to each well. The counting reagent was a solution of appropriate growth medium+2% Guava® ViaCount® Flex (Guava Technologies; Hayward, Calif.)+2% dimethyl sulfoxide (Guava Technologies; Hayward, Calif.). The resulting cell suspensions was aseptically transferred to an ultra-low cluster 96-well microplate for counting in Guava® EasyCyte® instrument (Guava Technologies; Hayward, Calif.).

Inoculation and Culture in 24-Well Microplates.

Cryopreserved vials of hUTC were thawed, washed and resuspended in growth media. Growth medium was prepared using both Hayflick and Adv. DMEM/F12, supplemented with 15%, 7.5% and 3.75%. 1.00E+04 hUTC per well were added to four wells per condition. Each well contained 1 ml growth medium. The plate was cultured in 5% $CO_2$, 37° C. tissue culture incubators for 96 hours.

Harvest and Counting of Cells from 24-Well Microplates.

The cell containing 24-well microplate was removed from incubation and media removed by aseptic aspiration. The cells were washed with 1 ml PBS per well; PBS was removed by aseptic aspiration and 500 µl TrypLE™ Select was added. The cells were incubated for 5 minutes at 37° C., after which, the plate was lightly tapped to dislodge the cells. The cell suspensions were pipetted several times and then transferred to a 1.5 mL Eppendorf tube containing 500 µl Guava® ViaCount® reagent (Guava Technologies, Haywood, Calif.) for counting in the Guava® PCA instrument (Guava Technologies, Haywood, Calif.).

Inoculation and Culture in T75 Flasks.

Cryopreserved vials of hUTC were thawed, washed and resuspended in growth medium. 3.75E+05 hUTC were added to T75 flasks containing 15 ml media. Flasks were cultured in 5% $CO_2$, 37° C. tissue culture incubators for three to four days.

Harvest and Passage of Cells from T75 Flasks.

Cell containing T75 flasks are removed from incubation and the media removed by aseptic aspiration. The cells were washed with 5 ml PBS; the PBS was removed by aseptic aspiration and replaced with 1 ml TrypLE™ Select. The cells were incubated for 5 minutes at 37° C., after which, the flasks were lightly tapped to dislodge adherent cells. 5 ml of medium was added to each flask and the cell suspension was transferred by pipette to a conical tube. The cells were centrifuged for 5 minutes at 300 rcf, the supernatant decanted, the cells re-suspended in growth medium and an aliquot was obtained for cell counting. After counting, an aliquot calculated to contain 3.75E+05 cells was obtained and used to inoculate new T75 flasks containing fresh media.

Inoculation and Culture in 100 ml Spinner Flasks.

Cryopreserved vials of hUTC were thawed, washed and resuspended in growth media. 3.1E+06 hUTC were added to 1.2 g of HILLEX® II ($5.0 \times 10^3$ cells per $cm^2$) in a 100 ml spinner flask, containing 100 ml media and placed on a spinner plate set to 60 rpm, continuous rotation. Spinner flasks on spinner plates were placed in 5% $CO_2$, 37° C. tissue culture incubators and incubated for three to four days.

Passage of 100 ml Spinner Flask Culture to 500 ml Spinner Flask Culture.

A 100 ml spinner flask was removed from its spinner plate and the microcarriers were allowed to settle. The supernatant medium was removed by aspiration and the remaining microcarrier pack with adherent cells was resuspended in 20 ml fresh growth medium. The microcarriers with adherent cells were then aseptically transferred by pipette to a 500 ml spinner flask containing 480 ml fresh growth medium and 4.8 g HILLEX® II microcarriers (6 g final microcarrier content or 12 g/L final microcarrier concentration). The spinner flask was then placed on a spinner plate set to 60 rpm, continuous rotation. Spinner flasks on spinner plates were placed in 5% $CO_2$, 37° C. tissue culture incubators and incubated for three to four days.

Passage of One 500 ml Spinner Flask Culture to Five 500 ml Spinner Flask Cultures.

A 500 ml spinner flask was removed from its spinner plate and the microcarriers were allowed to settle. The supernatant medium was removed by aspiration and the remaining microcarrier pack with adherent cells was resuspended in 50 ml fresh growth media. A 10 ml aliquot of the microcarriers with adherent cells was then aseptically transferred by pipette to five separate 500 ml spinner flasks, each containing 490 ml fresh growth medium and 4.8 g HILLEX® II microcarriers (6 g final microcarrier content or 12 g/L final microcarrier concentration). The spinner flasks were then placed on a spinner plate set to 60 rpm, continuous rotation. Spinner flasks on spinner plates were placed in 5% $CO_2$, 37° C. tissue culture incubators and incubated for three to four days.

Harvest of Cells Adherent to HILLEX® II Microcarriers.

A spinner flask was removed from its spinner plate and the microcarriers with adherent cells were allowed to settle by gravity. The supernatant medium was aseptically aspirated. A volume of PBS equal to the working volume of the spinner flask was added to the spinner flask and the microcarriers were allowed to settle by gravity. Upon settling of the microcarriers, the PBS was aseptically aspirated and a volume of TrypLE™ Select equal to ⅕th the working volume was added to the spinner flask. The spinner flask was then incubated on spinner plate for 10 minutes at 60 rpm, continuous rotation. The spinner flask was removed from its spinner plate and the microcarriers were allowed to settle by gravity. Using a 25 ml serological pipette, the microcarrier/TrypLE™ Select solution was agitated by pipetting up and down ~10 times to dissociate residual adherent cells from the microcarriers. The cell-containing supernatant was collected by repeated pipetting and transfers to multiple conical tubes fitted with 100 μm cell strainers. The tubes were filled with 5 ml FBS prior to collection cell suspensions. After collecting the cell suspension, the tubes were centrifuged for 5 minutes at 300 rcf, the supernatant decanted, and the cells re-suspended in growth medium.

Viability Staining.

A 1 ml aliquot of medium and microcarriers were transferred to a 15 ml conical tube, were the microcarriers were allowed to settle by gravity. Medium was removed by aseptic aspiration and replaced with 1 ml Live/Dead staining solution (Molecular Probes cat. no. L3224; Carlsbad, Calif.) and incubated from 15 minutes at 37° C. After incubation, a 20 μl aliquot was applied to a glass microscope slide and observed by fluorescent microscopy: viable cells stained green and non-viable cells stained red. Microscopic fields were manually analyzed to evaluate the distribution of viable cells adhered to the microcarriers. At least three microscopic fields were evaluated and the approximate percentage of viable cells was counted.

Culture Cell Counts—TrypLE™ Select Assay

A 5 ml (100 ml spinner flask) or 10 ml (500 ml spinner flask) aliquot of homogenous microcarrier suspension was obtained from a spinner flask vessel and transferred to a 15 ml tube. The microcarriers were allowed to gravity separate and the supernatant medium was removed by aseptic aspiration. The microcarriers were washed once with 10 ml PBS, the microcarriers allowed to gravity separate and the PBS supernatant removed by aseptic aspiration. The microcarriers were incubated for ten minutes at 37° C. in TrypLE™ Select. After incubation, 5 ml of PBS was added and the microcarriers were allowed to gravity separate. The cell containing supernatant was collected by repeated pipetting and transfer to multiple conical tubes pre-loaded with 1 ml FBS. The tubes were centrifuged for 5 minutes at 300 rcf, the supernatant decanted, the cells re-suspended in growth medium and an aliquot was used determine cell count using a Guava® PCA instrument (Guava Technologies, Haywood, Calif.).

Flow Cytometry.

Harvested hUTC were analyzed by flow cytometry using a Becton-Dickinson FACSCalibur™ instrument (Becton Dickinson, San Jose, Calif.) to determine the cell surface marker profile using methods stated in U.S. Publication No. 2005/0054098. All antibodies purchased from BD PharMingen (San Diego, Calif.).

Results

TABLE 30

Average cells per well from hUTC isolate 120304 in 96-well microplate format proliferation assay. Media used were Hayflick with serially diluted FBS and Advanced DMEM/F12 + 4.00 mM GlutaMAX ® with serially diluted FBS.

| Percent | Adv. DMEM/F12 | | Hayflick | |
|---|---|---|---|---|
| Serum | Average | Std. Dev. | Average | Std. Dev. |
| 0.00% | 2661.16 | 1312.842734 | 1980.2 | 937.425602 |
| 0.94% | 6202.46 | 3287.721263 | 3091.395 | 1430.894211 |
| 1.88% | 7868.305 | 1156.451927 | 4837.44 | 1898.341291 |
| 3.75% | 13997.585 | 3026.211963 | 8495.72 | 2900.665154 |
| 7.50% | 22594.545 | 3077.802473 | 10955.07 | 4451.859442 |
| 15.00% | 25934.625 | 2867.961465 | 19292.82 | 7723.45867 |

TABLE 31

Average cells per well from hUTC isolate 120304 in 24-well microplate format proliferation assay. Media used were Hayflick or Advanced DMEM/F12 + 4.00 mM GlutaMAX ® with 3.75%, 7.5% or 15% FBS.

| Percent | Adv. DMEM/F12 | | Hayflick | |
|---|---|---|---|---|
| Serum | Average | Std. Dev. | Average | Std. Dev. |
| 15% | 91816.75 | 6584.55 | 68708.03 | 3541.25 |
| 7.50% | 60571.39 | 4648.66 | 39028.80 | 5490.94 |
| 3.75% | 42613.14 | 2493.51 | 21731.38 | 760.79 |

TABLE 32

Continuous culture of hUTC isolate 120304 on T75 (flask 1) in Advanced DMEM/F12 + 4.0 mM GlutaMAX ® + 7.5% FBS.
Advanced DMEM/F12 + 4.00 mM GlutaMAX + 7.5% FBS- Flask 1

| Passage | Seeded | Yield | Expansion | Doubling | Total Doublings | Time (Days) | Hours/Doubling |
|---|---|---|---|---|---|---|---|
| 0 | | 3.75E+05 | 1.00 | | | | |
| 1 | 3.75E+05 | 4.54E+06 | 12.11 | 3.60 | 3.60 | 3.00 | 20.01 |
| 2 | 3.75E+05 | 3.49E+06 | 9.31 | 3.22 | 6.82 | 4.00 | 29.83 |
| 3 | 3.75E+05 | 1.68E+06 | 4.48 | 2.16 | 8.98 | 3.00 | 33.28 |
| 4 | 3.75E+05 | 2.07E+06 | 5.51 | 2.46 | 11.44 | 4.00 | 38.97 |
| 5 | 3.75E+05 | 1.95E+06 | 5.21 | 2.38 | 13.82 | 3.00 | 30.23 |
| 6 | 3.75E+05 | 2.84E+06 | 7.57 | 2.92 | 16.75 | 4.00 | 32.87 |
| 7 | 3.75E+05 | 1.42E+06 | 3.79 | 1.92 | 18.67 | 3.00 | 37.48 |
| 8 | 3.75E+05 | 1.44E+06 | 3.84 | 1.94 | 20.61 | 4.00 | 49.46 |
| 9 | 3.75E+05 | 1.91E+06 | 5.09 | 2.35 | 22.96 | 4.00 | 40.88 |
| 10 | 3.75E+05 | 1.05E+06 | 2.80 | 1.49 | 24.44 | 4.00 | 64.63 |
| 11 | 3.75E+05 | 1.77E+06 | 4.72 | 2.24 | 26.68 | 3.00 | 32.16 |

TABLE 33

Continuous culture of hUTC isolate 120304 on T75 (flask 2)
in Advanced DMEM/F12 + 4.0 mM GlutaMAX ® + 7.5% FBS.
Advanced DMEM/F12 + 4.00 mM GlutaMAX + 7.5% FBS- Flask 2

| Passage | Seeded | Yield | Expansion | Doubling | Total Doublings | Time (Days) | Hours/Doubling |
|---|---|---|---|---|---|---|---|
| 0 |  | 3.75E+05 | 1.00 |  |  |  |  |
| 1 | 3.75E+05 | 3.87E+06 | 10.32 | 3.37 | 3.37 | 3.00 | 21.38 |
| 2 | 3.75E+05 | 3.62E+06 | 9.65 | 3.27 | 6.64 | 4.00 | 29.35 |
| 3 | 3.75E+05 | 2.01E+06 | 5.36 | 2.42 | 9.06 | 3.00 | 29.72 |
| 4 | 3.75E+05 | 2.21E+06 | 5.89 | 2.56 | 11.62 | 4.00 | 37.52 |
| 5 | 3.75E+05 | 2.04E+06 | 5.43 | 2.44 | 14.06 | 3.00 | 29.50 |
| 6 | 3.75E+05 | 2.21E+06 | 5.89 | 2.56 | 16.62 | 4.00 | 37.51 |
| 7 | 3.75E+05 | 2.17E+06 | 5.79 | 2.53 | 19.15 | 3.00 | 28.43 |
| 8 | 3.75E+05 | 3.09E+06 | 8.24 | 3.04 | 22.19 | 4.00 | 31.55 |
| 9 | 3.75E+05 | 2.39E+06 | 6.37 | 2.67 | 24.87 | 4.00 | 35.93 |
| 10 | 3.75E+05 | 1.71E+06 | 4.56 | 2.19 | 27.06 | 4.00 | 43.85 |
| 11 | 3.75E+05 | 7.57E+05 | 2.02 | 1.01 | 28.07 | 3.00 | 71.05 |

TABLE 34

Continuous culture of hUTC isolate 120304 on T75 (flask 3)
in Advanced DMEM/F12 + 4.0 mM GlutaMAX ® + 7.5% FBS
Advanced DMEM/F12 + 4.00 mM GlutaMAX + 7.5% FBS- Flask 3

| Passage | Seeded | Yield | Expansion | Doubling | Total Doublings | Time (Days) | Hours/Doubling |
|---|---|---|---|---|---|---|---|
| 0 |  | 3.75E+05 | 1.00 |  |  |  |  |
| 1 | 3.75E+05 | 4.08E+06 | 10.88 | 3.44 | 3.44 | 3.00 | 20.91 |
| 2 | 3.75E+05 | 3.54E+06 | 9.44 | 3.24 | 6.68 | 4.00 | 29.64 |
| 3 | 3.75E+05 | 2.37E+06 | 6.32 | 2.66 | 9.34 | 3.00 | 27.07 |
| 4 | 3.75E+05 | 2.10E+06 | 5.60 | 2.48 | 11.83 | 4.00 | 38.64 |
| 5 | 3.75E+05 | 2.45E+06 | 6.53 | 2.71 | 14.53 | 3.00 | 26.60 |
| 6 | 3.75E+05 | 3.84E+06 | 10.24 | 3.36 | 17.89 | 4.00 | 28.60 |
| 7 | 3.75E+05 | 2.83E+06 | 7.55 | 2.92 | 20.81 | 3.00 | 24.69 |
| 8 | 3.75E+05 | 3.22E+06 | 8.59 | 3.10 | 23.91 | 4.00 | 30.95 |
| 9 | 3.75E+05 | 1.84E+06 | 4.91 | 2.29 | 26.20 | 4.00 | 41.83 |
| 10 | 3.75E+05 | 1.95E+06 | 5.20 | 2.38 | 28.58 | 4.00 | 40.36 |
| 11 | 3.75E+05 | 1.03E+06 | 2.75 | 1.46 | 30.04 | 3.00 | 49.39 |

TABLE 35

Continuous culture of hUTC isolate 120304 on T75 (flask 1) in growth media
Growth Media- Flask 1

| Passage | Seeded | Yield | Expansion | Doubling | Total Doublings | Time (Days) | Hours/Doubling |
|---|---|---|---|---|---|---|---|
| 0 |  | 3.75E+05 | 1.00 |  |  |  |  |
| 1 | 3.75E+05 | 3.12E+06 | 8.32 | 3.06 | 3.06 | 3.00 | 23.56 |
| 2 | 3.75E+05 | 4.72E+06 | 12.59 | 3.65 | 6.71 | 4.00 | 26.27 |
| 3 | 3.75E+05 | 1.87E+06 | 4.99 | 2.32 | 9.03 | 3.00 | 31.06 |
| 4 | 3.75E+05 | 2.66E+06 | 7.09 | 2.83 | 11.85 | 4.00 | 33.97 |
| 5 | 3.75E+05 | 1.84E+06 | 4.89 | 2.29 | 14.15 | 3.00 | 31.43 |
| 6 | 3.75E+05 | 4.23E+06 | 11.28 | 3.50 | 17.64 | 4.00 | 27.46 |
| 7 | 3.75E+05 | 1.55E+06 | 4.13 | 2.05 | 19.69 | 3.00 | 35.17 |
| 8 | 3.75E+05 | 1.97E+06 | 5.25 | 2.39 | 22.08 | 4.00 | 40.11 |
| 9 | 3.75E+05 | 2.20E+06 | 5.87 | 2.55 | 24.63 | 4.00 | 37.61 |
| 10 | 3.75E+05 | 2.04E+06 | 5.44 | 2.44 | 27.08 | 4.00 | 39.29 |
| 11 | 3.75E+05 | 1.69E+06 | 4.51 | 2.17 | 29.25 | 3.00 | 33.15 |

TABLE 36

Continuous culture of hUTC isolate 120304 on T75 (flask 2) in growth media
Growth Media- Flask 2

| Passage | Seeded | Yield | Expansion | Doubling | Total Doublings | Time (Days) | Hours/Doubling |
|---|---|---|---|---|---|---|---|
| 0 |  | 3.75E+05 | 1.00 |  |  |  |  |
| 1 | 3.75E+05 | 4.27E+06 | 11.39 | 3.51 | 3.51 | 3.00 | 20.52 |
| 2 | 3.75E+05 | 3.60E+06 | 9.60 | 3.26 | 6.77 | 4.00 | 29.42 |
| 3 | 3.75E+05 | 2.88E+06 | 7.68 | 2.94 | 9.71 | 3.00 | 24.48 |
| 4 | 3.75E+05 | 2.88E+06 | 7.67 | 2.94 | 12.65 | 4.00 | 32.66 |
| 5 | 3.75E+05 | 1.95E+06 | 5.21 | 2.38 | 15.03 | 3.00 | 30.24 |

TABLE 36-continued

Continuous culture of hUTC isolate 120304 on T75 (flask 2) in growth media
Growth Media- Flask 2

| Passage | Seeded | Yield | Expansion | Doubling | Total Doublings | Time (Days) | Hours/Doubling |
|---|---|---|---|---|---|---|---|
| 6 | 3.75E+05 | 3.65E+06 | 9.73 | 3.28 | 18.32 | 4.00 | 29.24 |
| 7 | 3.75E+05 | 1.45E+06 | 3.87 | 1.95 | 20.27 | 3.00 | 36.90 |
| 8 | 3.75E+05 | 1.71E+06 | 4.56 | 2.19 | 22.46 | 4.00 | 43.85 |
| 9 | 3.75E+05 | 1.91E+06 | 5.09 | 2.35 | 24.81 | 4.00 | 40.88 |
| 10 | 3.75E+05 | 2.90E+06 | 7.73 | 2.95 | 27.76 | 4.00 | 32.53 |
| 11 | 3.75E+05 | 9.67E+05 | 2.58 | 1.37 | 29.12 | 3.00 | 52.68 |

TABLE 37

Continuous culture of hUTC isolate 120304 on T75 (flask 2) in growth media
Growth Media- Flask 3

| Passage | Seeded | Yield | Expansion | Doubling | Total Doublings | Time (Days) | Hours/Doubling |
|---|---|---|---|---|---|---|---|
| 0 |  | 3.75E+05 | 1.00 |  |  |  |  |
| 1 | 3.75E+05 | 3.61E+06 | 9.63 | 3.27 | 3.27 | 3.00 | 22.04 |
| 2 | 3.75E+05 | 3.24E+06 | 8.64 | 3.11 | 6.38 | 4.00 | 30.86 |
| 3 | 3.75E+05 | 2.92E+06 | 7.79 | 2.96 | 9.34 | 3.00 | 24.32 |
| 4 | 3.75E+05 | 2.64E+06 | 7.05 | 2.82 | 12.16 | 4.00 | 34.07 |
| 5 | 3.75E+05 | 1.67E+06 | 4.45 | 2.15 | 14.31 | 3.00 | 33.45 |
| 6 | 3.75E+05 | 4.58E+06 | 12.21 | 3.61 | 17.92 | 4.00 | 26.59 |
| 7 | 3.75E+05 | 8.95E+05 | 2.39 | 1.25 | 19.17 | 3.00 | 57.37 |
| 8 | 3.75E+05 | 2.16E+06 | 5.76 | 2.53 | 21.70 | 4.00 | 38.00 |
| 9 | 3.75E+05 | 1.93E+06 | 5.15 | 2.36 | 24.06 | 4.00 | 40.62 |
| 10 | 3.75E+05 | 3.85E+06 | 10.27 | 3.36 | 27.42 | 4.00 | 28.57 |
| 11 | 3.75E+05 | 7.07E+05 | 1.89 | 0.91 | 28.34 | 3.00 | 78.70 |

TABLE 38

Continuous culture of hUTC isolate 120304 in spinner flasks
in Advanced DMEM/F12 + 4.0 mM GlutaMAX ® + 7.5% FBS
Advanced DMEM/F12 + 4.00 mMGlutaMAX ® + 7.5% FBS in spinner flask culture

| Passage | Seeded | Yield | Expansion | Doubling | Total Doublings | Time (Days) | Hours/Doubling |
|---|---|---|---|---|---|---|---|
| 0 |  | 1.91E+06 | 1.00 |  |  |  |  |
| 1 | 1.91E+06 | 7.70E+06 | 4.03 | 2.01 | 2.01 | 3.00 | 35.80 |
| 2 | 7.70E+06 | 8.59E+07 | 11.15 | 3.48 | 5.49 | 4.00 | 27.59 |
| 3 | 1.72E+07 | 1.02E+08 | 5.91 | 2.56 | 8.05 | 4.00 | 37.45 |

TABLE 39

Continuous culture of hUTC isolate 120304 in spinner flasks in growth media
Growth Media in spinner flask culture

| Passage | Seeded | Yield | Expansion | Doubling | Total Doublings | Time (Days) | Hours/Doubling |
|---|---|---|---|---|---|---|---|
| 0 |  | 1.98E+06 | 1.00 |  |  |  |  |
| 1 | 1.98E+06 | 5.82E+06 | 2.94 | 1.56 | 1.56 | 3.00 | 46.29 |
| 2 | 5.82E+06 | 5.10E+07 | 8.76 | 3.13 | 4.69 | 4.00 | 30.66 |
| 3 | 1.02E+07 | 5.76E+07 | 5.65 | 2.50 | 7.19 | 4.00 | 38.43 |

TABLE 40

Comparison of cell surface proteins expression by
hUTC expanded in Advanced DMEM/F12 + 4.0 mM
GlutaMAX ® + 7.5% FBS or growth media.

| Cell Surface Marker | Growth Media | Advanced DMEM/F12 |
|---|---|---|
| CD10 | (+) | (+) |
| CD13 | (+) | (+) |
| CD31 | (−) | (−) |
| CD34 | (−) | (−) |

TABLE 40-continued

Comparison of cell surface proteins expression by
hUTC expanded in Advanced DMEM/F12 + 4.0 mM
GlutaMAX ® + 7.5% FBS or growth media.

| Cell Surface Marker | Growth Media | Advanced DMEM/F12 |
|---|---|---|
| CD44 | (+) | (+) |
| CD45 | (−) | (−) |
| CD73 | (+) | (+) |
| CD90 | (+) | (+) |
| CD117 | (−) | (−) |
| CD140 | (−) | (−) |
| HLA-A, B, C | (+) | (+) |
| HLA-DQ, DP, DR | (−) | (−) |

Cryopreserved hUTC isolate 120304 was thawed and expanded in replicate T75 flasks with reduced serum growth media for eleven passages. The hours per population doubling for each replicate T75 flask was consistent from passage to passage, indicating stable logarithmic growth. Statistical analysis by one-way ANOA of all hours per population doubling data points show no significant difference in hUTC growth kinetics for all data points (p=0.821). The cell surface protein expression of hUTC expanded in reduced serum media was consistent with hUTCs expanded in standard growth media.

Also, cryopreserved hUTC isolate 120304 was thawed and expanded on Hillex II microcarrier containing spinner flasks with reduced serum growth media for three passages. The hours per population doubling for each spinner flask was consistent from passage to passage, indicating stable logarithmic growth. Statistical analysis by two-sample T-test of the average hours per population doubling show no significant difference the hUTC growth kinetics between the two medias tested. (p=0.424).

This data demonstrated the ability of hUTC to be expanded in static T flask or microcarrier culture systems with reduced serum media over multiple passages in a stable, consistent manner and maintain its phenotypic cell surface protein expression.

Example 9

Expansion of hUTC on HILLEX® II Microcarriers in a 3 L Bioreactor

The goal of this study was to expanded human umbilical tissue derived cells (hUTC) adherent to HILLEX® II microcarriers in a bench scale bioreactor over multiple population doublings. The ability to expand hUTC on HILLEX® II over multiple population doublings in a bench scale bioreactor will serve a model bioprocessing system to be scale-up for large-scale production of hUTC for cell therapy applications. hUTC isolate CNTO 2476 expanded to approximately 70% confluence on HILLEX® II microcarriers in a 500 ml spinner flask were used to inoculate a 3 L bioreactor containing additional media and HILLEX® II microcarriers. The cells were cultured in the bioreactor for five days with aliquots taken to calculate a mid-run cell counts.

The hUTC achieved approximately six population doubling in five days. The hours per population doubling was indicative of stable logarithmic growth. The pH of the system was successfully maintained at 7.0 by a $CO_2$ air overlay and without sparging. The DO of the system was successfully maintained at 40% by oxygen air overlay and without sparging.

This data demonstrates the ability of hUTC to be expanded on HILLEX® II in a bench scale bioreactor. This model bioprocessing system can be scale-up for large-scale production of hUTC for cell therapy application.

The goal of this study was to expanded human umbilical tissue derived cells (hUTC) adherent to HILLEX® II microcarriers in a bench scale bioreactor over multiple population doublings. The ability to expand hUTC on HILLEX® II over multiple population doublings in a bench scale bioreactor will serve a model bioprocessing system to be scale-up for large-scale production of hUTC for cell therapy applications. hUTC isolate CNTO 2476 expanded to approximately 70% confluence on HILLEX® II microcarriers in a 500 ml spinner flask were used to inoculate a 3 L bioreactor containing additional media and HILLEX® II microcarriers. The cells were cultured in the bioreactor for five days with aliquots taken to calculate a mid-run cell counts.

Materials and Methods

Cells.

Cryopreserved expanded human umbilical cord tissue cells (hUTC) isolate CNTO 2476 lot 25126078 PD 7 used.

Growth Media.

Dulbecco's Modified Eagles Media (DMEM)-low glucose without phenol red (Gibco—Grand Island, N.Y.), 15% fetal bovine serum (FBS) (HyClone—Logan Utah), 4.0 mM GlutaMAX® (Gibco—Grand Island, N.Y.), Harvest Reagent.

1× TrypLE™ Select (Gibco—Grand Island, N.Y.), 10× TrypLE™ Select (Gibco—Grand Island, N.Y.), Microcarriers.

HILLEX® II (SoloHill Inc.—Ann Arbor, Mich.) microcarriers were hydrated in DI water for at least 30 minutes autoclaved. HILLEX® II microcarriers were used at a concentration of 12 g/L.

Bioreactor.

3 L jacketed bioreactor (Applikon, Inc., Foster City, Calif.) with a B-DCU controller (Sartorius BBI, Bethlehem, Pa.).

Bioreactor Inoculation.

6 g of microcarriers with attached cells at approximately 70% confluence yielded from a 500 ml spinner flask were aseptically transferred to a 3 L bioreactor containing 30 g HILLEX® II and approximately 2 L growth media. Additional growth media was then added to bring the final volume to 3 L.

Bioreactor Settings.

The bioreactor impeller was set to 85-100 RPM. The pH set point was 7.0 and controlled with CO2 addition. The dissolved oxygen (DO) was allowed to drift down from 100% to a 40% DO set point and maintained by oxygen addition. The air overlay was set to 50 ccm and no sparging was used.

Harvest of Cells Adherent to HILLEX® II Microcarriers.

The bioreactor impeller was turned off and the microcarriers with adherent cells were allowed to settle by gravity. The media supernatant was pumped out through a dip tube positioned above the settled microcarriers. 3 L of PBS was pumped into the bioreactor and the microcarriers were allowed to settle by gravity. The PBS supernatant was pumped out through a dip tube positioned above the settled microcarriers. 500 ml of 1× TrypLE™ select and 50 ml of 10× TrypLE™ select was then pumped into the bioreactor. The bioreactor impeller was tuned on for 10 minutes at 65 rpm. The impeller was turned off and the microcarriers were allowed to settle by gravity. The cell containing supernatant pumped out through a dip tube positioned above the settled microcarriers into a transfer container pre-loaded with a small amount of FBS. 1 L of PBS was then pumped into to the bioreactor to re-suspend any remaining cells. The cell containing supernatant pumped out through a dip tube positioned above the settled microcarriers into a transfer container pre-loaded with FBS. All cell-containing supernatant was transferred to multiple 500 ml conical tubes. The tubes were centrifuged for 5 minutes at 300 rcf, the supernatant decanted, the cells re-suspended in growth media and aliquot obtained for cell counting.

In Culture Cell Counts—TrypLE™ Assay

A 5 ml (100 ml spinner flask) or 10 ml (500 ml spinner flask) aliquot of homogenous microcarrier suspension was obtained from spinner flask vessel and transferred to a 15 ml tube. The microcarriers were allowed to gravity separate and the supernatant was removed by aspiration. The microcarriers were washed once with 10 ml PBS, the microcarriers allowed to gravity separate, and the PBS supernatant removed by aspiration. The microcarriers were incubated for ten minutes at 37° C. in TrypLE™ select. After incubation, 5 ml of PBS is added and the microcarriers are allowed to gravity separate. The cell containing supernatant is collect by repeated pipetting and transfer to multiple conical tubes pre-loaded with 1 ml FBS. The tubes were centrifuged for 5 minutes at 300 rcf, the supernatant decanted, the cells re-suspended in growth media, and an aliquot is used determine cell count.

Results

TABLE 41

Continuous culture of hUTC isolate CNTO 2476 on HILLEX ® II microcarriers.
CNTO 2476 on Hillex II

| aliquot | Seeded | Yield | Doubling | Total Doublings | Time (Days) | Hours/ Doubling |
|---|---|---|---|---|---|---|
| innoculation | | 7.99E+06 | | | | |
| mid-run sample | 7.99E+06 | 7.47E+07 | 3.22 | 3.22 | 3.00 | 22.33 |
| mid-run sample | 7.47E+07 | 2.88E+08 | 1.94 | 5.17 | 1.00 | 12.34 |
| harvest | 2.88E+08 | 6.15E+08 | 1.10 | 6.27 | 1.00 | 21.89 | hUTC isolate CNTO 2476 adherent at 70% confluence to 6 g of HILLEX® II were used to inoculate a 3 L bioreactor. The pH of the system was successfully maintained at 7.0 by a $CO_2$ air overlay and without sparging. The DO of the system was successfully maintained at 40% by oxygen air overlay and without sparging. The hUTC achieved approximately six population doubling in five days. The hours per population doubling was indicative of stable logarithmic growth. This data demonstrates the ability of hUTC to be expanded on HILLEX® II in a bench scale bioreactor. This model bioprocessing system can be scale-up for large-scale production of hUTC for cell therapy application.

Example 10

Expansion of hUTC on HILLEX® II Microcarriers at Concentrations of 12-24 Grams/Liter The goal of this study was to continuously culture expanded human umbilical tissue derived cells (hUTC) adherent to HILLEX® II microcarriers at multiple microcarrier concentrations in spinner flasks. The ability to expand hUTC on microcarriers at various microcarrier concentrations will provide greater flexibility and options for large-scale production of hUTC for cell therapy applications. Cryopreserved hUTC isolate 120304 was thawed and used to immediately inoculate spinner flasks containing HILLEX® II microcarriers at concentrations of 12, 16, 20, or 24 g/L and were continuously cultured over multiple passages.

hUTC isolate 120304 cryopreserved at population doubling 12.8 was able to be thawed, and expanded on HILLEX® II microcarriers for seven passages. The hours per population doubling was for each microcarrier concentration was consistent from passage to passage, indicating stable logarithmic growth. Statistical analysis by one-way ANOA of all hours per population doubling data points show no significant difference the hUTC growth kinetics for all conditions tested. (p=0.277). This data demonstrated the ability of hUTC to be expanded over seven passages on microcarriers in a stable, consistent manner.

The goal of this study was to continuously culture expanded human umbilical tissue derived cells (hUTC) adherent to HILLEX® II microcarriers at multiple microcarrier concentrations in spinner flasks. The ability to expand hUTC on microcarriers at various microcarrier concentrations will provide greater flexibility and options for large-scale production of hUTC for cell therapy applications. Cryopreserved hUTC isolate 120304 was thawed and used to immediately inoculate spinner flasks containing HILLEX® II microcarriers at concentrations of 12, 16, 20, or 24 g/L and were continuously cultured over multiple passages.

Materials and Methods

Cells.

Cryopreserved expanded human umbilical cord tissue cells (hUTC) isolate 12034 population doubling (PD) 12.

Growth Media.

Dulbecco's Modified Eagles Media (DMEM)-low glucose (Gibco—Grand Island, N.Y.), 15% fetal bovine serum (FBS) (HyClone—Logan Utah), penicillin/streptomycin (P/S) (Gibco—Grand Island, N.Y.), Betamercaptoethanol (BME) (Sigma—St. Louis, Mo.).

Microcarriers.

HILLEX® II microcarriers were hydrated in DI water for at least 30 minutes autoclaved. HILLEX® II microcarriers were used at a concentration of 12, 16, 20, and 24 g/L. (1 g HILLEX® II=515 cm2 surface area).

Spinner Flask.

100 ml and 500 ml single-use, disposable spinner flasks (Corning, Inc.—Corning, N.Y.) were used.

Inoculation and Culture in 100 ml Spinner Flask.

100 ml spinner flasks were loaded with 100 ml growth media and appropriate concentration of microcarriers to achieve 12, 16, 20, or 24 grams of HILLEX® II per liter. Cryopreserved vials of hUTC were thawed, washed and resuspended in growth media. The appropriate numbers of cells were added to each 100 ml spinner flask to achieve $5.0 \times 10^3$ cells per $cm^2$. Cell loaded spinner flask were placed on a spinner plate set to 60-rpm continuous rotation. Spinner plates placed in 5% $CO_2$, 37° C. tissue culture incubators and incubated for three to four days.

Passage of Culture From One 100 ml Spinner Flask to One 500 ml Spinner Flask.

100 ml spinner flask was removed from spinner plate and the microcarriers were allowed to settle. The media supernatant was removed by aspiration. The remaining microcarrier pack with adherent cells was resuspended in 20 ml fresh growth media. The microcarriers with adherent cells were then aseptically transferred by pipette to a 500 ml spinner flask containing 480 ml fresh growth media and 4.8 g HILLEX®II (6 g final microcarrier content) or 1.2 g Cytodex® 1 (1.5 g final microcarrier content). The spinner flask was then placed on a spinner plate set to 60-rpm continuous rotation. Spinner plates placed in 5% $CO_2$, 37° C. tissue culture incubators and incubated for three to four days.

Passage of Culture From one 100 ml Spinner Flask to One 100 ml Spinner Flask.

100 ml spinner flask was removed from spinner plate and the microcarriers were allowed to settle. The media supernatant is removed by aspiration. The remaining microcarrier pack with adherent cells was resuspended in 50 ml fresh growth media. A 10 ml aliquots of the microcarriers with adherent cells were then aseptically transferred by pipette to a separate 100 ml spinner flask each containing 90 ml fresh growth media and 0.96 g HILLEX® II (1.2 g final microcarrier content). The spinner flasks were then placed on a spinner plate set to 60-rpm continuous rotation. Spinner plates placed in 5% $CO_2$, 37° C. tissue culture incubators and incubated for three to four days.

Harvest of Cells Adherent to HILLEX® II Microcarriers.

The spinner flask was removed from spinner plate and the microcarriers with adherent cells were allowed to settle by gravity. The media supernatant was removed by aspiration. A volume of PBS equal to the working volume of the spinner flask was added to the spinner flask and the microcarriers were allowed to settle by gravity. A volume of TrypLE™ select equal to ⅕th the working volume was added to the spinner flask. The spinner flask was then incubated on spinner plate for 10 minutes at 60 rpm. The spinner flask was removed from spinner plate and the microcarriers were allowed to settle by gravity. Using a 25 ml serological pipette, the microcarriers-TrypLE™ select solution was agitated by pipetting up and down ~10 times to dissociate residual adherent cells from the microcarriers. The cell containing supernatant is collect by repeated pipetting and transfer to multiple conical tubes pre-loaded with 5 ml FBS and a 100 nm filter unit inserted in the tube opening. The tubes were centrifuged for 5 minutes at 300 rcf, the supernatant decanted, and the cells re-suspended in growth media.

Viability Staining.

A 1 ml aliquot of media and microcarriers were transferred to a 15 ml conical tube and the microcarriers were allowed to separate by gravity. Media was removed by aspiration and replaced with 1 ml Live/Dead staining solution (Molecular Probes cat. no. L3224) and incubated from 15 minutes at 37° C. After incubation a 20 µl aliquot was applied to a glass microscope slide and observed by fluorescent microscopy. Live cells stain green. Microscopic fields were manually analyzed to evaluate the distribution of viable cells adhered to the microcarriers. At least three microscopic fields were evaluated and the approximate percentage of viable cells was counted.

In Culture Cell Counts—TrypLE™ Assay

A 5 ml (100 ml spinner flask) or 10 ml (500 ml spinner flask) aliquot of homogenous microcarrier suspension was obtained from spinner flask vessel and transferred to a 15 ml tube. The microcarriers were allowed to gravity separate and the supernatant was removed by aspiration. The microcarriers were washed once with 10 ml PBS, the microcarriers allowed to gravity separate, and the PBS supernatant removed by aspiration. The microcarriers were incubated for ten minutes at 37° C. in TrypLE™ select. After incubation, 5 ml of PBS is added and the microcarriers are allowed to gravity separate. The cell containing supernatant is collect by repeated pipetting and transfer to multiple conical tubes pre-loaded with 1 ml FBS. The tubes were centrifuged for 5 minutes at 300 rcf, the supernatant decanted, the cells re-suspended in growth media, and an aliquot is used determine cell count using a Guava® PCA instrument (Guava Technologies, Haywood, Calif.).

Results

TABLE 42

Continuous culture of hUTC isolate 120304 on 12 g/L HILLEX ® II microcarriers.
12 g/L Hillex II

| Passage | Seeded | Yield | Doubling | Total Doublings | Time (Days) | Hours/ Doubling |
| --- | --- | --- | --- | --- | --- | --- |
| 1 | | 5.15E+06 | | 12.00 | | |
| 2 | 1.03E+06 | 1.78E+07 | 4.11 | 16.11 | 4.00 | 23.37 |
| 3 | 3.55E+06 | 2.23E+07 | 2.65 | 18.76 | 3.00 | 27.19 |
| 4 | 4.45E+06 | 2.95E+07 | 2.73 | 21.48 | 4.00 | 35.18 |
| 5 | 5.90E+06 | 1.53E+07 | 1.37 | 22.86 | 3.00 | 52.37 |
| 6 | 3.06E+06 | 1.30E+07 | 2.09 | 24.95 | 4.00 | 46.00 |
| 7 | 1.23E+07 | 3.46E+07 | 1.49 | 26.44 | 3.00 | 48.25 |

TABLE 43

Continuous culture of hUTC isolate 120304 on 16 g/LHILLEX ® II microcarriers.
16 g/L Hillex II

| Passage | Seeded | Yield | Doubling | Total Doublings | Time (Days) | Hours/ Doubling |
| --- | --- | --- | --- | --- | --- | --- |
| 1 | | 4.05E+06 | | 12.00 | | |
| 2 | 8.10E+05 | 7.80E+06 | 3.27 | 15.27 | 4.00 | 29.38 |
| 3 | 1.56E+06 | 8.74E+06 | 2.49 | 17.75 | 3.00 | 28.97 |
| 4 | 1.75E+06 | 1.93E+07 | 3.47 | 21.22 | 4.00 | 27.70 |
| 5 | 3.86E+06 | 1.85E+07 | 2.26 | 23.48 | 3.00 | 31.85 |
| 6 | 3.70E+06 | 1.54E+07 | 2.06 | 25.54 | 4.00 | 46.66 |
| 7 | 1.46E+07 | 4.70E+07 | 1.69 | 27.22 | 3.00 | 42.69 |

TABLE 44

Continuous culture of hUTC isolate 120304 on 20 g/L HILLEX ® II microcarriers
20 g/L Hillex II

| Passage | Seeded | Yield | Doubling | Total Doublings | Time (Days) | Hours/ Doubling |
|---|---|---|---|---|---|---|
| 1 |  | 4.39E+06 |  | 12.00 |  |  |
| 2 | 8.78E+05 | 1.23E+07 | 3.81 | 15.81 | 4.00 | 25.18 |
| 3 | 2.47E+06 | 1.19E+07 | 2.27 | 18.08 | 3.00 | 31.72 |
| 4 | 2.38E+06 | 1.78E+07 | 2.90 | 20.99 | 4.00 | 33.05 |
| 5 | 3.56E+06 | 1.66E+07 | 2.22 | 23.21 | 3.00 | 32.41 |
| 6 | 3.32E+06 | 2.04E+07 | 2.62 | 25.83 | 4.00 | 36.65 |
| 7 | 1.94E+06 | 3.86E+07 | 4.31 | 30.14 | 3.00 | 16.69 |

TABLE 45

Continuous culture of hUTC isolate 120304 on 24 g/L HILLEX ® II microcarriers
24 g/L Hillex II

| Passage | Seeded | Yield | Doubling | Total Doublings | Time (Days) | Hours/ Doubling | Total Time |
|---|---|---|---|---|---|---|---|
| 1 |  | 7.49E+06 |  | 12.00 |  |  | 0.00 |
| 2 | 1.50E+06 | 2.25E+07 | 3.91 | 15.91 | 4.00 | 24.56 | 4.00 |
| 3 | 4.50E+06 | 1.74E+07 | 1.95 | 17.86 | 3.00 | 36.94 | 7.00 |
| 4 | 3.48E+06 | 1.17E+07 | 1.75 | 19.61 | 4.00 | 54.81 | 11.00 |
| 5 | 2.34E+06 | 9.84E+06 | 2.07 | 21.68 | 3.00 | 34.75 | 14.00 |
| 6 | 1.97E+06 | 1.08E+07 | 2.46 | 24.14 | 4.00 | 39.08 | 18.00 |
| 7 | 1.03E+07 | 3.21E+07 | 1.64 | 25.78 | 3.00 | 43.87 | 21.00 | hUTC isolate 120304 cryopreserved at population doubling 12.8 was able to be thawed, and expanded on HILLEX® II microcarriers for seven passages. The hours per population doubling was for each microcarrier concentration was consistent from passage to passage, indicating stable logarithmic growth. Statistical analysis by one-way ANOA of all hours per population doubling data points show no significant difference the hUTC growth kinetics for all conditions tested. (p=0.277). This data demonstrated the ability of hUTC to be expanded over seven passages on microcarriers in a stable, consistent manner.

Example 11

Expansion of hUTC on Microcarriers in Continuous Spinner Flask Culture

The goal of this study was to continuously culture expanded human umbilical tissue derived cells (hUTC) adherent to commercial microcarriers in spinner flasks over multiple population doublings. The ability to expand hUTC on microcarriers over multiple population doublings will serve a model system to be scale-up for large-scale production of hUTC for cell therapy applications. Two hUTC isolates, 120304-isolated, expanded and cryopreserved under research conditions, and CNTO 2476-isolated, expanded and cryopreserved under GMP conditions, were evaluated. The commercial microcarriers Cytodex® 1 or HILLEX® II were evaluated also. The cryopreserved cells were thawed and used to immediately inoculate spinner flask cultures. The cells were continuously cultured over multiple passages until the cell reached approximately population-doubling 30. hUTCs were also cultured statically in T225 flasks as a control.

hUTC isolate 120304 cryopreserved at population doubling 12.8 was able to be thawed, and expanded on Cytodex® 1 and HILLEX® II microcarriers to population doubling 28.6 and 28.7 respectively. The hours per population doubling was consistent from passage to passage, indicating stable logarithmic growth and was consistent with the T flask growth kinetics. hUTC isolate CNTO 2476 cryopreserved at population doubling 22.6 was able to be thawed, and expanded on Cytodex® 1 and HILLEX® II microcarriers to population doubling 33.2 and 31.0 respectively. The hours per population doubling was consistent from passage to passage, indicating stable logarithmic growth and was also consistent with the T flask growth kinetics. Statistical analysis by one-way ANOA of all hours per population doubling data points show no significant difference the hUTC growth kinetics for all conditions tested. (p=0.988). Also the cell surface protein expression remained consistent at final harvest for all conditions tested.

This data demonstrated the ability of hUTC to be expanded to approximately 30 population doublings on microcarriers in a stable, consistent manner that maintains the cell's surface protein phenotype. This model system can be scale-up for large scale production of hUTC for cell therapy application.

The goal of this study was to continuously culture expanded human umbilical tissue derived cells (hUTC) adherent to commercial microcarriers in spinner flasks over multiple population doublings. The ability to expand hUTC on microcarriers over multiple population doublings will serve a model system to be scale-up for large-scale production of hUTC for cell therapy applications. Two hUTC isolates, 120304 isolated, expanded and cryopreserved under research conditions, and CNTO 2476, isolated, expanded and cryopreserved under GMP conditions, were evaluated. The commercial microcarriers evaluated were Cytodex® 1 or HILLEX® II. The cryopreserved cells were thawed and used to immediately inoculate spinner flask cultures. The cells were continuously cultured over multiple passages until the cell reached population-doubling 30. hUTCs were also cultured statically in T225 flasks as a control.

Materials and Methods

Cells.

Cryopreserved expanded human umbilical cord tissue cells (hUTC) isolate 12034 population doubling (PD) 12 and hUTC isolate CNTO 2476 lot 25126078 PD 22 used.

Growth Media.

Dulbecco's Modified Eagles Media (DMEM)-low glucose (Gibco—Grand Island, N.Y.), 15% fetal bovine serum (FBS) (HyClone—Logan Utah), penicillin/streptomycin (P/S) (Gibco—Grand Island, N.Y.), Betamercaptoethanol (BME) (Sigma—St. Louis, Mo.)

Microcarriers.

Cytodex® 1 (GE Health Sciences—Piscataway, N.J.) microcarriers were hydrated in PBS for at least 3 hours and autoclaved. Cytodex® 1 microcarriers were used at a concentration of 3 g/L. HILLEX® II (SoloHill Inc.—Ann Arbor, Mich.) microcarriers were hydrated in deionized water for at least 30 minutes autoclaved. HILLEX® II microcarriers were used at a concentration of 12 g/L.

Spinner Flask.

100 ml and 500 ml single-use, disposable spinner flasks (Corning, Inc.—Corning, N.Y.) were used.

Inoculation and Culture in 100 ml Spinner Flask.

Cryopreserved vials of hUTC were thawed, washed and resuspended in growth media. $6.6 \times 10^6$ hUTC were added to 3000 mg of Cytodex® 1 ($5.0 \times 10^3$ cells per $cm^2$) in a 100 ml spinner flask containing 100 ml media and placed on a 37° C. tissue culture incubators and incubated for three to four days. Spinner plate was set to 60-rpm continuous rotation. $3.1 \times 10^6$ hUTC were added to 1.2 g of HILLEX® II ($5.0 \times 10^3$ cells per $cm^2$) in a 100 ml spinner flask containing 100 ml media and placed on a spinner plate set to 60-rpm continuous rotation. Spinner plates placed in 5% $CO_2$.

Passage of Culture From One 100 ml Spinner Flask to One 500 ml Spinner Flask.

100 ml spinner flask was removed from spinner plate and the microcarriers were allowed to settle. The media supernatant is removed by aspiration. The remaining microcarrier pack with adherent cells was resuspended in 20 ml fresh growth media. The microcarriers with adherent cells were then aseptically transferred by pipette to a 500 ml spinner flask containing 480 ml fresh growth media and 4.8 g HILLEX® II (6 g final microcarrier content) or 1.2 g Cytodex® 1 (1.5 g final microcarrier content). The spinner flask was then placed on a spinner plate set to 60-rpm continuous rotation. Spinner plates placed in 5% $CO_2$, 37° C. tissue culture incubators and incubated for three to four days.

Passage of Culture Form One 500 ml Spinner Flask to Five 500 ml Spinner Flasks.

500 ml spinner flask was removed from spinner plate and the microcarriers were allowed to settle. The media supernatant is removed by aspiration. The remaining microcarrier pack with adherent cells was resuspended in 50 ml fresh growth media. Five separate 10 ml aliquots of the microcarriers with adherent cells were then aseptically transferred by pipette to five separate 500 ml spinner flasks each containing 490 ml fresh growth media and 4.8 g HILLEX®II (6 g final microcarrier content) or 1.2 g Cytodex® 1 (1.5 g final microcarrier content). The spinner flasks were then placed on a spinner plate set to 60-rpm continuous rotation. Spinner plates placed in 5% $CO_2$, 37° C. tissue culture incubators and incubated for three to four days.

Harvest of Cells Adherent to Cytodex® 1 Microcarriers.

The 500 ml spinner flask was removed from spinner plate and the microcarriers with adherent cells were allowed to settle by gravity. The media supernatant was removed by aspiration. 500 ml of PBS was added to the spinner flask and the microcarriers were allowed to settle by gravity. The PBS supernatant was removed by aspiration. 500 ml of DMEM—low glucose was added to the spinner flask. The spinner flask was then incubated on spinner plate for 20 minutes at 60 rpm. The spinner flask was removed from spinner plate and the microcarriers were allowed to settle by gravity. The DMEM-low glucose supernatant was removed by aspiration. 500 ml of PBS was added to the spinner flask. The spinner flask was then incubated on spinner plate for 20 minutes at 60 rpm. The spinner flask was removed from spinner plate and the microcarriers were allowed to settle by gravity. The PBS supernatant was removed by aspiration. 250 ml TrypLE™ select was added to the spinner flask. The spinner flask was then incubated on spinner plate for 10 minutes at 60 rpm. The spinner flask was removed from spinner plate and the microcarriers were allowed to settle by gravity. Using a 50 ml serological pipette, the microcarriers-TrypLE™ select solution was agitated by pipetting up and down ~10 times to dissociate residual adherent cells from the microcarriers. 250 ml of PBS was then added to the spinner flask the microcarriers were allowed to settle by gravity. The cell containing supernatant is collect by repeated pipetting and transfer to multiple conical tubes pre-loaded with 5 ml FBS and a 100 nm filter unit inserted in the tube opening. The tubes were centrifuged for 5 minutes at 300 rcf, the supernatant decanted, and the cells re-suspended in growth media.

Harvest of Cells Adherent to HILLEX® II Microcarriers.

The 500 ml spinner flask was removed from spinner plate and the microcarriers with adherent cells were allowed to settle by gravity. The media supernatant was removed by aspiration. 500 ml of PBS was added to the spinner flask and the microcarriers were allowed to settle by gravity. 100 ml TrypLE™ select was added to the spinner flask. The spinner flask was then incubated on spinner plate for 10 minutes at 60 rpm. The spinner flask was removed from spinner plate and the microcarriers were allowed to settle by gravity. Using a 25 ml serological pipette, the microcarriers-TrypLE™ select solution was agitated by pipetting up and down ~10 times to dissociate residual adherent cells from the microcarriers. The cell containing supernatant is collect by repeated pipetting and transfer to multiple conical tubes pre-loaded with 5 ml FBS and a 100 µm filter unit inserted in the tube opening. The tubes were centrifuged for 5 minutes at 300 rcf, the supernatant decanted, and the cells re-suspended in growth media.

Viability Staining.

A 1 ml aliquot of media and microcarriers were transferred to a 15 ml conical tube and the microcarriers were allowed to separate by gravity. Media was removed by aspiration and replaced with 1 ml Live/Dead staining solution (Molecular Probes cat. no. L3224) and incubated from 15 minutes at 37° C. After incubation a 20 µl aliquot was applied to a glass microscope slide and observed by fluorescent microscopy. Live cells stain green. Microscopic fields were manually analyzed to evaluate the distribution of viable cells adhered to the microcarriers. At least three microscopic fields were evaluated and the approximate percentage of viable cells was counted.

In Culture Cell Counts—Nuclei Release Assay

A 5 ml (100 ml spinner flask) or 10 ml (500 ml spinner flask) aliquot of homogenous microcarrier suspension was obtained from spinner flask vessel and transferred to a 15 ml tube. The microcarriers were allowed to gravity separate and the supernatant was removed by aspiration. The microcarriers were washed once with 10 ml PBS, the microcarriers allowed to gravity separate, and the PBS supernatant removed by aspiration. The microcarriers were incubated for one hour at 37° C. in nuclei release solution (0.1M citric acid (Sigma—

St. Louis, Mo.) containing 0.1% w/v crystal violet (Sigma—St. Louis, Mo.)). After incubation, a 100 µl aliquot of the microcarrier containing nuclei release solution was added to 100 µl PBS. A 10 µl aliquot of this solution was then loaded into a hemocytometer and released nuclei counted.

In Culture Cell Counts—TrypLE™ Assay

A 5 ml (100 ml spinner flask) or 10 ml (500 ml spinner flask) aliquot of homogenous microcarrier suspension was obtained from spinner flask vessel and transferred to a 15 ml tube. The microcarriers were allowed to gravity separate and the supernatant was removed by aspiration. The microcarriers were washed once with 10 ml PBS, the microcarriers allowed to gravity separate, and the PBS supernatant removed by aspiration. The microcarriers were incubated for ten minutes at 37° C. in TrypLE™ select. After incubation, 5 ml of PBS is added and the microcarriers are allowed to gravity separate. The cell containing supernatant is collect by repeated pipetting and transfer to multiple conical tubes pre-loaded with 1 ml FBS. The tubes were centrifuged for 5 minutes at 300 rcf, the supernatant decanted, the cells re-suspended in growth media, and an aliquot is used determine cell count using a Guava® PCA instrument (Guava Technologies, Haywood, Calif.).

Static T-Flask Culture.

Cryopreserved vials of hUTC were thawed, washed and resuspended in growth media. The cells were cultured statically in T225 over multiple passages using methods stated in US2005/0054098.

Flow Cytometry.

Harvested hUTC were analyzed by flow cytometry using a Becton-Dickinson FACSCalibur™ instrument (Becton Dickinson, San Jose, Calif.) to determine the cell surface marker profile using methods stated in US2005/0054098. All antibodies purchased from BD PharMingen (San Diego, Calif.).

Results

TABLE 46

Continuous culture of hUTC isolate 120304 on Cytodex ® 1 microcarriers.
120304- Cytodex 1

| Passage | Seeded | Yield | Doubling | Total Doublings | time (days) | Hours/doubling |
|---|---|---|---|---|---|---|
| 6 (seed) |  | 5.32E+06 | 2.03E+00 | 1.28E+01 |  |  |
| 6 | 5.32E+06 | 4.71E+07 | 3.15E+00 | 1.59E+01 | 4.00 | 30.51 |
| 7 | 8.96E+06 | 7.30E+07 | 3.03E+00 | 1.89E+01 | 3.00 | 23.79 |
| 8 | 6.60E+06 | 3.30E+07 | 2.32E+00 | 2.12E+01 | 3.00 | 31.01 |
| 9 | 6.60E+06 | 3.90E+07 | 2.56E+00 | 2.38E+01 | 3.00 | 28.09 |
| 10 | 3.90E+07 | 2.17E+08 | 2.48E+00 | 2.63E+01 | 4.00 | 38.77 |
| 11 | 2.17E+08 | 1.10E+09 | 2.34E+00 | 2.86E+01 | 4.00 | 41.00 |

TABLE 47

Continuous culture of hUTC isolate 120304 on HILLEX ® II microcarriers.
120304- Hillex II

| Passage | Seeded | Yield | Doubling | Total Doublings | time (days) | Hours/doubling |
|---|---|---|---|---|---|---|
| 6 (seed) |  | 5.32E+06 | 2.03E+00 | 1.28E+01 |  |  |
| 6 | 5.32E+06 | 4.71E+07 | 3.15E+00 | 1.59E+01 | 4.00 | 30.51 |
| 7 | 8.96E+06 | 7.30E+07 | 3.03E+00 | 1.89E+01 | 3.00 | 23.79 |
| 8 | 3.00E+06 | 1.90E+07 | 2.66E+00 | 2.16E+01 | 3.00 | 27.04 |
| 9 | 3.80E+06 | 2.30E+07 | 2.60E+00 | 2.42E+01 | 3.00 | 27.72 |
| 10 | 2.30E+07 | 2.64E+08 | 3.52E+00 | 2.77E+01 | 4.00 | 27.27 |
| 11 | 2.11E+08 | 4.16E+08 | 9.79E−01 | 2.87E+01 | 3.00 | 73.52 |

TABLE 48

Continuous culture of hUTC isolate CNTO 2476 on Cytodex ® 1 microcarriers
CNTO 2476- Cytodex 1

| Passage | Seeded | Yield | doubling | Total Doublings | time (days) | hours/doubling |
|---|---|---|---|---|---|---|
| 6 (seed) |  | 6.30E+05 |  | 2.26E+01 |  |  |
| 6 | 6.30E+05 | 3.44E+06 | 2.45E+00 | 2.50E+01 | 3.00 | 29.40 |
| 7 | 3.44E+06 | 5.20E+07 | 3.92E+00 | 2.90E+01 | 4.00 | 24.50 |
| 8 | 4.00E+07 | 1.60E+08 | 2.00E+00 | 3.10E+01 | 3.00 | 36.00 |
| 8 | 1.60E+08 | 7.67E+08 | 2.26E+00 | 3.32E+01 | 4.00 | 42.46 |

TABLE 49

Continuous culture of hUTC isolate CNTO 2476 on HILLEX ® II microcarriers
CNTO 2476- Hillex II

| Passage | Seeded | Yield | doubling | Total Doublings | time (days) | hours/ doubling |
|---|---|---|---|---|---|---|
| 6 (seed) |  | 1.68E+06 |  | 2.26E+01 |  |  |
| 6 | 1.68E+06 | 1.29E+07 | 2.94E+00 | 2.55E+01 | 4.00 | 32.64 |
| 7 | 1.29E+07 | 5.30E+07 | 2.04E+00 | 2.76E+01 | 3.00 | 35.32 |
| 8 | 5.30E+07 | 5.60E+08 | 3.40E+00 | 3.10E+01 | 5.00 | 35.28 |

TABLE 50

Continuous culture of hUTC isolate 120304 in T225 flasks.
120304- T225 flask

| Passage | Seeded | Yield | doubling | Total Doublings | time (days) | hours/ doubling |
|---|---|---|---|---|---|---|
| 6 (seed) |  | 1.12E+07 | 2.03E+00 | 1.28E+01 |  |  |
| 6 | 1.12E+07 | 3.05E+07 | 1.45E+00 | 1.42E+01 | 2.00 | 33.21 |
| 7 | 2.20E+06 | 2.03E+07 | 3.21E+00 | 1.74E+01 | 4.00 | 29.94 |
| 8 | 3.75E+05 | 1.50E+06 | 2.00E+00 | 1.94E+01 | 3.00 | 36.00 |
| 9 | 3.75E+05 | 1.85E+06 | 2.30E+00 | 2.17E+01 | 4.00 | 41.69 |
| 10 | 3.75E+05 | 2.39E+06 | 2.67E+00 | 2.44E+01 | 3.00 | 26.95 |
| 11 | 7.50E+05 | 3.14E+06 | 2.07E+00 | 2.64E+01 | 4.00 | 46.47 |
| 12 | 3.14E+06 | 2.02E+07 | 2.69E+00 | 2.91E+01 | 3.00 | 26.81 |
| 13 | 2.02E+07 | 1.14E+08 | 2.50E+00 | 3.16E+01 | 4.00 | 38.45 |

TABLE 51

Comparison of cell surface proteins expression by hUTC expanded
on microcarrier and T-flasks and analyzed by flow cytometry.

| Cell Surface Marker | 120304 T225 flask | 120304 Cytodex 1 | 120304 Hillex II | CNTO 2476 Cytodex 1 | CNTO 2476 Hillex II |
|---|---|---|---|---|---|
| CD 10 | (+) | (+) | (+) | (+) | (+) |
| CD 13 | (+) | (+) | (+) | (+) | (+) |
| CD 31 | (−) | (−) | (−) | (−) | (−) |
| CD 34 | (−) | (−) | (−) | (−) | (−) |
| CD 44 | (+) | (+) | (+) | (+) | (+) |
| CD 45 | (−) | (−) | (−) | (−) | (−) |
| CD 73 | (+) | (+) | (+) | (+) | (+) |
| CD 90 | (+) | (+) | (+) | (+) | (+) |
| CD 117 | (−) | (−) | (−) | (−) | (−) |
| CD 141 | (−) | (−) | (−) | (−) | (−) |
| PDGFr-a | (+) | (+) | (+) | (+) | (+) |
| HLA-ABC | (+) | (+) | (+) | (+) | (+) |
| HLA-DRDPDQ | (−) | (−) | (−) | (−) | (−) | hUTC isolate 120304 cryopreserved at population doubling 12.8 was able to be thawed, and expanded on Cytodex® 1 and Hillex® II microcarriers to population doubling 28.6 and 28.7 respectively. The hours per population doubling was consistent from passage to passage, indicating stable logarithmic growth and was consistent with the T flask growth kinetics. hUTC isolate CNTO 2476 cryopreserved at population doubling 22.6 was able to be thawed, and expanded on Cytodex® 1 and Hillex® II microcarriers to population doubling 33.2 and 31.0 respectively. The hours per population doubling was consistent from passage to passage, indicating stable logarithmic growth and was also consistent with the T flask growth kinetics. Statistical analysis by one-way ANOA of all hours per population doubling data points show no significant difference the hUTC growth kinetics for all conditions tested. (p=0.988). Also the cell surface protein expression remained consistent at final harvest for all conditions tested. This data demonstrated the ability of hUTC to be expanded to approximately 30 population doublings on microcarriers in a stable, consistent manner that maintains the cell's surface protein phenotype. This model system can be scale-up for large scale production of hUTC for cell therapy application.

Example 12

Expansion of hUTC on Cytodex® 1 Microcarriers in a 3 L Bioreactor

The goal of this study was to expanded human umbilical tissue derived cells (hUTC) adherent to Cytodex® 1 microcarriers in a bench scale bioreactor over multiple population doublings. The ability to expand hUTC on Cytodex® 1 over multiple population doublings in a bench scale bioreactor will serve a model bioprocessing system to be scale-up for large-scale production of hUTC for cell therapy applications. hUTC isolate CNTO 2476 expanded to approximately 70% confluence on Cytodex® 1 microcarriers in a 500 ml spinner flask were used to inoculate a 3 L bioreactor containing additional media and Cytodex® 1 microcarriers. The cells were cultured in the bioreactor for six days with an aliquot taken at day 3 to calculate a mid-run cell count.

The hUTC achieved approximately three population doubling in six days. The pH of the system was successfully maintained at 7.0 by a $CO_2$ air overlay and without sparging. The DO of the system was successfully maintained at 40% by oxygen air overlay and without sparging. The proliferation of the culture from day 0 to day 3 was indicative of stable logarithmic growth. The reduced rate of proliferation seen from day 4 to 6 was most likely due to a depletion of nutrients (i.e. glucose) in the media by the increased cell mass.

This data demonstrates the ability of hUTC to be expanded on Cytodex® 1 in a bench scale bioreactor. This model bioprocessing system can be scale-up for large-scale production of hUTC for cell therapy application.

The goal of this study was to expanded human umbilical tissue derived cells (hUTC) adherent to Cytodex® 1 microcarriers in a bench scale bioreactor over multiple population doublings. The ability to expand hUTC on Cytodex® 1 over multiple population doublings in a bench scale bioreactor will serve a model bioprocessing system to be scale-up for large-scale production of hUTC for cell therapy applications. hUTC isolate CNTO 2476 expanded to approximately 70% confluence on Cytodex® 1 microcarriers in a 500 ml spinner flask were used to inoculate a 3 L bioreactor containing additional media and Cytodex® 1 microcarriers. The cells were cultured in the bioreactor for six days with a aliquot taken at day 3 to calculate a mid-run cell count.

Materials and Methods

Cells.

Cryopreserved expanded human umbilical cord tissue cells (hUTC) isolate CNTO 2476 lot 25126078 PD 7 used.

Growth Media.

Dulbecco's Modified Eagles Media (DMEM)-low glucose without phenol red (Gibco—Grand Island, N.Y.), 15% fetal bovine serum (FBS) (HyClone—Logan Utah), 4.0 mM GlutaMAX® (Gibco—Grand Island, N.Y.), Harvest Reagents.

1× TrypLE Select (Gibco—Grand Island, N.Y.), 10× TrypLE Select (Gibco—Grand Island, N.Y.), Microcarriers.

Cytodex® 1 (GE Health Sciences—Piscataway, N.J.) microcarriers were hydrated in PBS for at least 3 hours and autoclaved. Cytodex® 1 microcarriers were used at a concentration of 3 g/L.

Bioreactor.

3 L jacketed bioreactor (Applikon, Inc., Foster City, Calif.) with a B-DCU controller (Sartorius BBI, Bethlehem, Pa.)

Bioreactor Inoculation.

1.5 g of microcarriers with attached cells at approximately 70% confluence yielded from a 500 ml spinner flask were aseptically transferred to a 3 L bioreactor containing 7.5 g Cytodex® 1 and approximately 2 L growth media. Additional growth media was then added to bring the final volume to 3 L.

Bioreactor Settings.

The bioreactor impeller was 65 RPM. The pH set point was 7.0 and controlled with $CO_2$ addition. The dissolved oxygen (DO) was allowed to drift down from 100% to a 40% DO set point and maintained by oxygen addition. The air overlay was set to 25-150 ccm and no sparging was used.

Harvest of Cells Adherent to Cytodex 1 Microcarriers.

The bioreactor impeller was turned off and the microcarriers with adherent cells were allowed to settle by gravity. The media supernatant was pumped out through a dip tube positioned above the settled microcarriers. 3 L of PBS was pumped into the bioreactor and the microcarriers were allowed to settle by gravity. The PBS supernatant was pumped out through a dip tube positioned above the settled microcarriers. 3 L of DMEM—low glucose was pumped into to the bioreactor. The bioreactor impeller was tuned on for 30 minutes at 65 rpm. The impeller was then turned off and the microcarriers were allowed to settle by gravity. The DMEM-low glucose supernatant was pumped out through a dip tube positioned above the settled microcarriers. 3 L of PBS was then pumped into to the bioreactor. The bioreactor impeller was tuned on for 20 minutes at 65 rpm. The impeller was then turned off and the microcarriers were allowed to settle by gravity. The PBS supernatant was pumped out through a dip tube positioned above the settled microcarriers. 1 L of 1× TrypLE™ select and 50 ml of 10× TrypLE™ select was then pumped into the bioreactor. The bioreactor impeller was tuned on for 20 minutes at 65 rpm. The impeller was turned off and the microcarriers were allowed to settle by gravity. The cell containing supernatant pumped out through a dip tube positioned above the settled microcarriers into a transfer container pre-loaded with a small amount of FBS. 1.5 L of PBS was then pumped into to the bioreactor to re-suspend any remaining cells. The cell containing supernatant pumped out through a dip tube positioned above the settled microcarriers into a transfer container pre-loaded with FBS. All cell-containing supernatant was transferred to multiple 500 ml conical tubes. The tubes were centrifuged for 5 minutes at 300 rcf, the supernatant decanted, the cells re-suspended in growth media and aliquot obtained for cell counting.

In Culture Cell Counts—Nuclei Release Assay

An aliquot of homogenous microcarrier suspension was obtained from spinner flask vessel and transferred to a 15 ml tube. The microcarriers were allowed to gravity separate and the supernatant was removed by aspiration. The microcarriers were washed once with 10 ml PBS, the microcarriers allowed to gravity separate, and the PBS supernatant removed by aspiration. The microcarriers were incubated for one hour at 37° C. in nuclei release solution (0.1M citric acid (Sigma—St. Louis, Mo.) containing 0.1% w/v crystal violet (Sigma—St. Louis, Mo.)). After incubation, a 100 µl aliquot of the microcarrier containing nuclei release solution was added to 100 µl PBS. A 10 µl aliquot of this solution was then loaded into a hemocytometer and released nuclei counted.

Results

TABLE 52

Continuous culture of hUTC isolate CNTO 2476 on Cytodex ® 1 microcarriers.
CNTO 2476 on Cytodex 1

| aliquot | Seeded | Yield | Doubling | Total Doublings | Time (Days) | Hours/ Doubling |
|---|---|---|---|---|---|---|
| innoculation | | 8.99E+07 | | | | |
| mid-run sample | 8.99E+07 | 5.38E+08 | 2.58 | 2.58 | 3.00 | 27.89 |
| harvest | 5.38E+08 | 6.73E+08 | 0.32 | 2.90 | 3.00 | 223.21 | hUTC isolate CNTO 2476 adherent at 70% confluence to 1.5 g of Cytodex® 1 were used to inoculate a 3 L bioreactor. The pH of the system was successfully maintained at 7.0 by a $CO_2$ air overlay and without sparging. The DO of the system was successfully maintained at 40% by oxygen air overlay and without sparging. The hUTC achieved approximately three population doubling in six days. The proliferation of the culture from day 0 to day 3 was indicative of stable logarithmic growth. The reduced rate of proliferation seen from day 4 to 6 was most likely due to a depletion of nutrients (i.e. glucose) in the media by the increased cell mass.

This data demonstrates the ability of hUTC to be expanded on Cytodex® 1 in a bench scale bioreactor. This model bioprocessing system can be scale-up for large-scale production of hUTC for cell therapy application.

What is claimed:

1. A method of culturing anchorage-dependent postpartum-derived cells comprising:
   providing at least one anchorage-dependent postpartum-derived cell;
   providing a cell growth medium for growing the postpartum-derived cell;
   providing at least one microcarrier for attachment of the anchorage-dependent postpartum-derived cell;
   contacting and culturing the anchorage-dependent cell with the microcarrier in the presence of the growth medium under conditions permitting attachment and growth of the cell, wherein the conditions permitting attachment and growth of the cell comprise constant stirring at microcarrier culture initiation and during culturing,
   wherein the resulting cultured cell is phenotypically the same as corresponding anchorage-dependent postpartum-derived cells grown in static cultures for all of the following markers: CD 10, CD 13, CD31, CD34, CD44, CD45, CD73, CD90, CD117, CD141, PDGFr-α, HLA-A, HLA-B, HLA-C, HLA-DR, HLA-DP, and HLA-DQ; and
   wherein the postpartum-derived cell is selected from the group consisting of an umbilical derived cell and a placental derived cell.

2. The method of claim 1, wherein the cells are umbilical derived cells.

3. The method of claim 1, wherein the cells are placental derived cells.

4. The method of claim 1 wherein the microcarrier contains a bioactive agent.

5. The method of claim 1 further comprising a second cell type co-cultured with said anchorage-dependent postpartum-derived cells.

6. The method of claim 1 wherein the microcarrier is comprised of a material selected from the group consisting of glass, ceramic, metal, polystyrene, poly(monostearoylglyceride co-succinic acid), poly-D,L-lactide-co-glycolide, and sodium hyaluronate.

7. The method of claim 1 wherein the microcarrier is protein free.

8. The method of claim 1 wherein the microcarrier comprises a textured surface.

9. The method of claim 1 wherein the microcarrier possesses a microcurrent or is paramagnetic.

10. The method of claim 1 wherein the microcarrier is porous.

11. The method of claim 10 wherein the porous microcarrier is comprised of a material selected from the group consisting of glass, ceramic, metal, polystyrene, poly(monostearoylglyceride co-succinic acid), poly-D,L-lactide-co-glycolide, and sodium hyaluronate.

12. The method of claim 10 wherein the porous microcarrier is protein free.

13. The method of claim 10 wherein the porous microcarrier comprises a textured surface.

14. The method of claim 10 wherein the porous microcarrier is uncoated.

15. The method of claim 10 wherein the porous microcarrier is coated with poly(monostearoylglyceride co-succinic acid), poly-D,L-lactide-co-glycolide, sodium hyaluronate, fibronectin, laminin, elastin, lysine, n-isopropyl acrylamide, vitronectin, or collagen.

16. The method of claim 1 wherein the phenotype of the cultured cells comprises CD10+, CD13+, CD31−, CD34−, CD44+, CD45−, CD73+, CD90+, CD117−, CD141−, PDGFr-α+, HLA-A+, HLA-B+, HLA-C+, HLA-DR−, HLA-DP−, and HLA-DQ−.

17. The method of claim 1 which results in at least about five population doublings over about twenty days.

18. The method of claim 1 wherein the doubling time for the population is less than about 100 hours.

19. The method of claim 18 wherein the doubling time for the population is less than about 70 hours.

20. The method of claim 1 wherein conditions which permit attachment and growth of the anchorage-dependent postpartum-derived cell comprise a temperature of about 37° C.

21. The method of claim 20 wherein conditions further comprise a spinner flask or bioreactor.

22. The method of claim 1 wherein the cell growth medium comprises a serum concentration from about 7% to about 15%.

23. The method of claim 1 wherein the microcarrier is uncoated.

24. The method of claim 1 wherein the microcarrier is coated with poly(monostearoylglyceride co-succinic acid), poly-D,L-lactide-co-glycolide, sodium hyaluronate, fibronectin, laminin, elastin, lysine, n-isopropyl acrylamide, vitronectin, or collagen.

* * * * *